(12) United States Patent
Fallaux et al.

(10) Patent No.: US 6,395,519 B1
(45) Date of Patent: *May 28, 2002

(54) MEANS AND METHODS FOR NUCLEIC ACID DELIVERY VEHICLE DESIGN AND NUCLEIC ACID TRANSFER

(75) Inventors: Frits J. Fallaux, Leiderdorp; Robert C. Hoeben, Leiden; Abraham Bout, Moerkapelle; Domenico Valerio, Leiden; Alex J. van der Eb, Oegstgeest; Govert Schouten, Leiden, all of (NL)

(73) Assignee: IntroGene B.V., Leiden (NL)

( * ) Notice: Subject to any disclaimer, the term of this patent is extended or adjusted under 35 U.S.C. 154(b) by 0 days.

This patent is subject to a terminal disclaimer.

(21) Appl. No.: 09/298,745

(22) Filed: Apr. 23, 1999

Related U.S. Application Data

(63) Continuation-in-part of application No. 08/793,170, filed as application No. PCT/NL96/00244 on Jun. 14, 1996, now Pat. No. 5,994,128.

(30) Foreign Application Priority Data

Jun. 15, 1995 (EP) ............................................. 95201611
Jun. 26, 1995 (EP) ............................................. 95201728

(51) Int. Cl.⁷ .......................... C12N 5/10; C12N 15/10; C12N 15/63; C12N 15/64; C12N 15/861
(52) U.S. Cl. ................ 435/91.42; 435/69.1; 435/320.1; 435/325; 435/366; 435/369; 435/91.4; 435/455; 435/456; 435/457; 435/371; 435/368
(58) Field of Search .............................. 435/69.1, 320.1, 435/235.1, 325, 366, 369, 5, 6, 91.4, 91.42, 455, 456, 457, 371, 368

(56) References Cited

U.S. PATENT DOCUMENTS

| | | |
|---|---|---|
| 4,405,712 A | 9/1983 | Vande Woude et al. |
| 4,497,796 A | 2/1985 | Salser et al. |
| 4,727,028 A | 2/1988 | Santerre et al. |
| 4,740,463 A | 4/1988 | Weinberg et al. |
| 5,190,931 A | 3/1993 | Inouye |
| 5,208,149 A | 5/1993 | Inouye |
| 5,378,618 A | 1/1995 | Sternberg et al. |
| 5,518,913 A | 5/1996 | Massie et al. |
| 5,545,522 A | 8/1996 | Van Gelder et al. |

(List continued on next page.)

FOREIGN PATENT DOCUMENTS

| | | |
|---|---|---|
| AU | A-28533/95 | 3/1996 |
| CA | 2117668 | 9/1955 |
| CA | 2053187 | 4/1993 |
| EP | 95201611.1 | 6/1995 |
| EP | 95201728.3 | 6/1995 |
| FR | 2 707 664 | 1/1995 |
| WO | WO 94/12649 | 6/1994 |
| WO | WO 94/23582 | 10/1994 |
| WO | WO 94/26914 | 11/1994 |
| WO | WO 94/28152 | 12/1994 |
| WO | WO 95/00655 | 1/1995 |
| WO | WO 95/02697 | 1/1995 |
| WO | WO 95/27071 | 10/1995 |
| WO | WO 96/16676 | 6/1996 |
| WO | WO 96/18418 | 6/1996 |
| WO | WO 96/33280 | 10/1996 |
| WO | WO 96/40955 | 12/1996 |
| WO | WO 97/00326 | 1/1997 |
| WO | WO 97/00947 | 1/1997 |
| WO | WO 97/04119 | 2/1997 |
| WO | Wo 97/05255 | 2/1997 |

OTHER PUBLICATIONS

Amalfitano et al., "Improved adenovirus packaging cell lines to support the growth of replication–defective gene–delivery vectors", *Proc. Natl. Acad. Sci. USA*, 93:3352–3356, Apr. 1996.

(List continued on next page.)

*Primary Examiner*—David Guzo
(74) *Attorney, Agent, or Firm*—TraskBritt

(57) ABSTRACT

Cells capable of at least, in part, complementing adenovirus E2A function of an adenovirus defective in E2A function. Such cells include a nucleic acid encoding adenovirus E2A or a functional part, derivative and/or analogue thereof, integrated into the genome of the cell. Preferably, the cell has E2A nucleic acid derived from a temperature sensitive adenovirus such as adenovirus ts125. Methods for producing an adenovirus particle containing an adenovirus vector with a finctional deletion of E2A are also disclosed. Such a method involves providing a cell as previously described with the functionally deleted adenovirus vector, culturing the cell, and harvesting the virus particle. The functional deletion can comprise a deletion of at least part of the nucleic acid encoding E2A. In such a method, the nucleic acid encoding adenovirus E2A in the genome of the cell preferably has no sequence overlap with the vector which leads to replication competent adenovirus and/or to the formation of an adenovirus vector comprising E2A function. In the method, the adenovirus vector preferably further comprises a functional deletion of E1-region encoding nucleic acid. Adenovirus vectors comprising a functional deletion of adenovirus E2A, preferably a deletion of at least part of the nucleic acid encoding E2A are also disclosed. Preparations of adenovirus vector containing adenovirus particles wherein the adenovirus vector comprises a functional deletion of E2A are also disclosed. Such an adenovirus vector preferably further includes a deletion of nucleic acid encoding E1-region proteins, and may be free of adenovirus vectors comprising E2A function. Methods for providing cells of an individual with a nucleic acid of interest, without risk of administering simultaneously a replication competent adenovirus vector, comprising administering the individual one of the previously described preparations are also disclosed.

16 Claims, 10 Drawing Sheets

U.S. PATENT DOCUMENTS

| | | | |
|---|---|---|---|
| 5,652,224 | A | 7/1997 | Wilson et al. |
| 5,670,488 | A | 9/1997 | Gregory et al. |
| 5,707,618 | A | 1/1998 | Armentano et al. |
| 5,753,500 | A | 5/1998 | Shenk et al. |
| 5,837,511 | A | 11/1998 | Falck-Pedersen et al. |
| 5,994,106 | A | 11/1999 | Kovesdi et al. |
| 5,994,128 | A | 11/1999 | Fallaux et al. |
| 6,033,908 | A | 3/2000 | Bout et al. |
| 6,040,174 | A | 3/2000 | Imler et al. |

OTHER PUBLICATIONS

Amalfitano et al., "Isolation and characterization of packaging cell lines that coexpress the adenovirus E1, DNA polymerase, and preterminal proteins: implications for gene therapy", *Gene Therapy*, 4:258–263, 1997.

Armentano et al., "Characterization of an Adenovirus Gene Transfer Vector Containing an E4 Deletion", *Human Gene Therapy*, 6:1343–1353, Oct. 1995.

Brough et al., "A Gene Transfer Vector–Cell Line System for Complete Functional Complementation of Adenovirus Early Regions E1 and E4", *Journal of Virology*, 70(9):6497–6501, Sep. 1996.

Brough et al., "Construction, Characterization, and Utilization of Cell Lines Which Inducibly Express the Adenovirus DNA–Binding Protein", *Virology*, 190:624–634, 1992.

Brough et al., Stable Cell Lines for Complementation of Adenovirus Early Regions E1, E2A and E4; Abstract Book CSH Conference On Gene Therapy, 42, 1996.

Caravokyri et al., "Constitutive Episomal Expression of Polypeptide IX (pIX) in a 293–Based Cell Line Complements the Deficiency of pIX Mutant Adenovirus Type 5", *Journal of Virology*, 69(11):6627–6633, Nov. 1995.

Fallaux et al., "Characterization of 911: A New Helper Cell Line for the Titration and Propagation of Early Region 1–Deleted Adenoviral Vectors", *Human Gene Therapy*, 7:215–222, 1996.

Fisher et al., "Recombinant Adenovirus Deleted of All Viral Genes for Gene Therapy of Cystic Fibrosis", *Virology*, 217:11–22, 1996.

Gao et al., "Biology of Adenovirus Vectors with E1 and E4 Deletions for Liver–Directed Gene Therapy", *Journal of Virology*, 70(12):8934–8943, Dec. 1996.

Gorziglia et al., "Elimination of both E1 and E2a from Adenovirus Vectors Further Improves Prospects for In Vivo Human Gene Therapy", *Journal of Virology*, 70(6):4173–4178, Jun. 1996.

Hardy et al., "Construction of Adenovirus Vectors through Cre–lox Recombination", *Journal of Virology*, 71(3):1842–1849, Mar. 1997.

Hehir et al., "Molecular Characterization of Replication–Competent Variants of Adenovirus Vectors and Genome Modifications To Prevent Their Occurence", *Journal of Virology*, 70(12):8459–8467, Dec. 1996.

Imler et al., "Novel complementation cell lines derived from human lung carcinoma A549 cells support the growth of E1–deleted adenovirus vectors", *Gene Therapy*, 3:75–84, 1996.

Kornberg, Arthur, "DNA Replication", W.H. Freeman and Company, San Francisco, 8 pages.

Krougliak et al., "Development of Cell Lines Capable of Complementing E1, E4, and Protein IX Defective Adenovirus Type 5 Mutants", *Human Gene Therapy*, 6:1575–1586, Dec. 1995.

Lieber et al., "Recombinant Adenoviruses and Large Deletions Generated by Cre–Mediated Excision Exhibit Different Biological Properties Compared with First–Generation Vectors In Vitro and In Vivo", *Journal of Virology*, 70:8944–8960, Dec. 1996.

Ngo et al., "in The Protein Folding Problem and Tertiary Structure Prediction", Merz et al., (ed.), Birkhauser, Boston, MA, pp. 433 and 492–495, 1994.

Sabatie et al., "Process Development for the Production of Second Generation Adenovirus Vectors for Gene Transfer in Clinical Protocols", Abstract Book 14th Meeting on Animal Cell Technology, BI–3, 1996.

Schaack et al., "Adenovirus Type 5 Precursor Terminal Protein–Expressing 293 and HeLa Cell Lines", *Journal of Virology*, 69(7):4079–4085, Jul. 1995.

Vanhaesebroeck et al., *Virology*, 176(2), pp. 362–368, Jun. 1990.

Wang et al., "A packaging cell line for propagation of recombinant adenovirus vectors containing two lethal gene–region deletions", *Gene Therapy*, 2:775–783, 1995.

Yeh et al., "Efficient Dual Transcomplementation of Adenovirus E1 and E4 Regions from a 293–Derived Cell Line Expressing a Minimal E4 Functional Unit", *Journal of Virology*, 70(1):559–565, Jan. 1996.

Zhou et al., "Development of a Complementing Cell Line and a System for Construction of Adenovirus Vectors with E1 and E2a Deleted", *Journal of Virology*, 70(1):7030–7038, Oct. 1996.

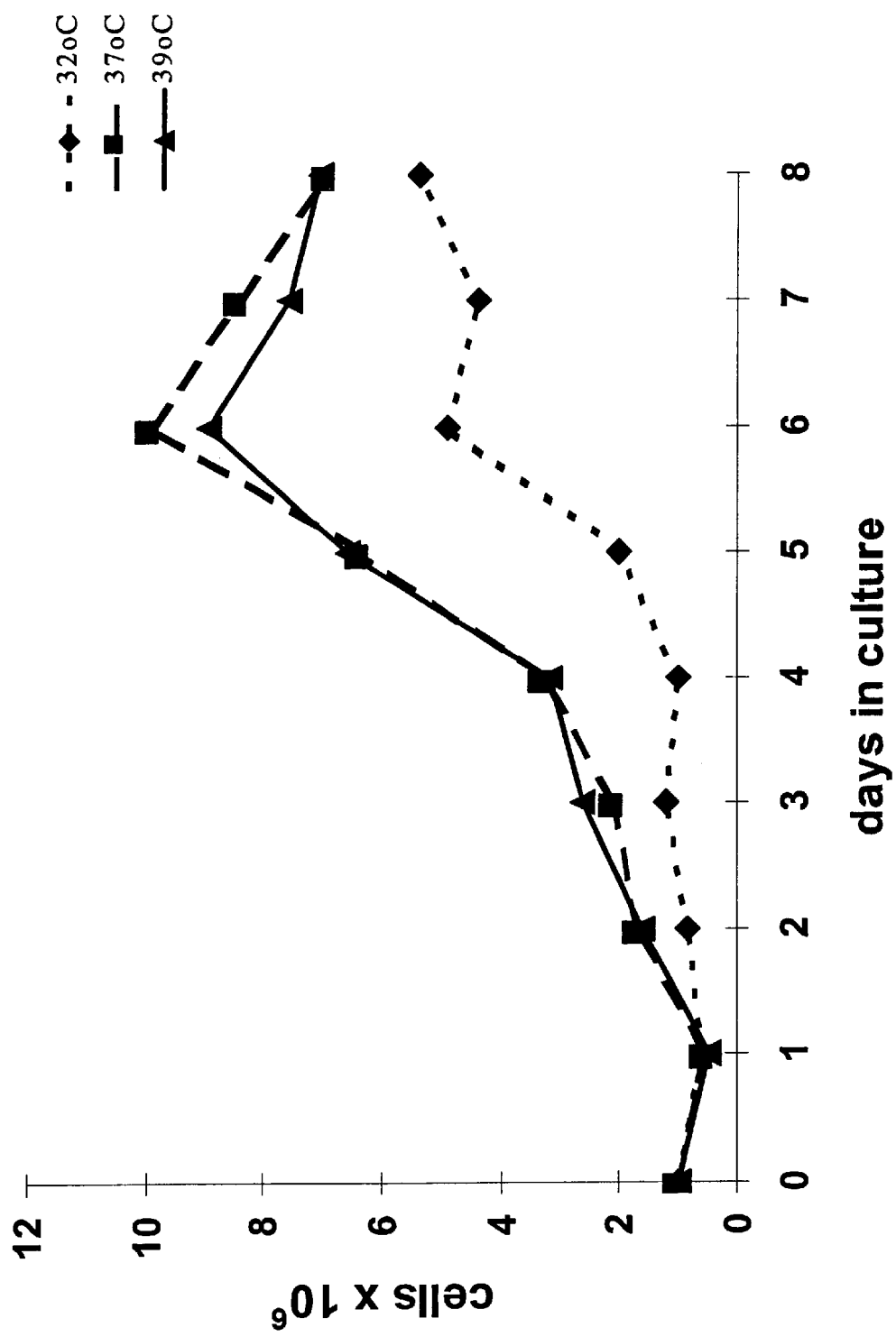
Figure 1  Temperature dependent growth of PER.C6

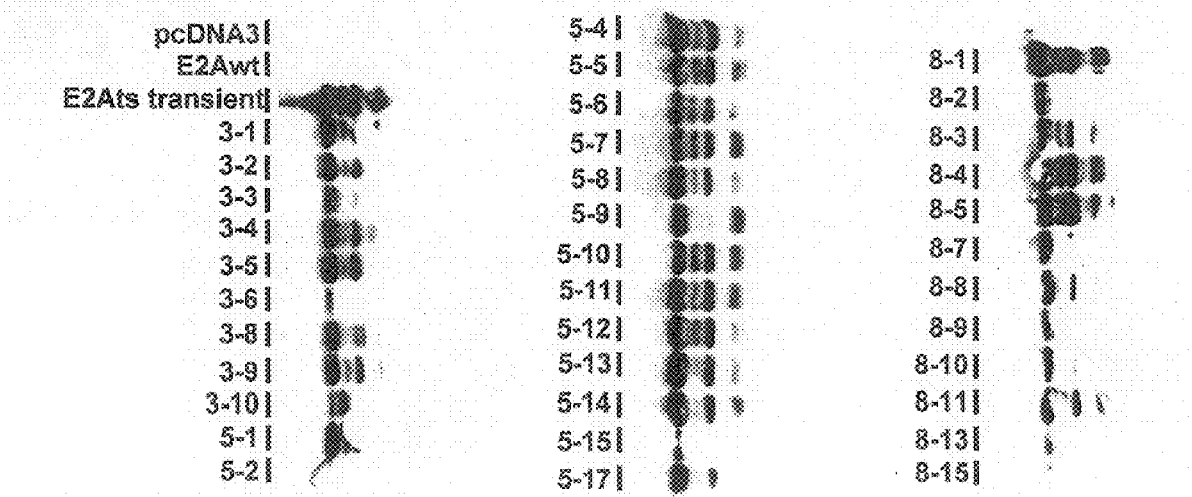
Figure 2: DBP levels in PER.C6 cells transfected with pcDNA3, pcDNA3wtE2A or pcDNA3ts125E2A

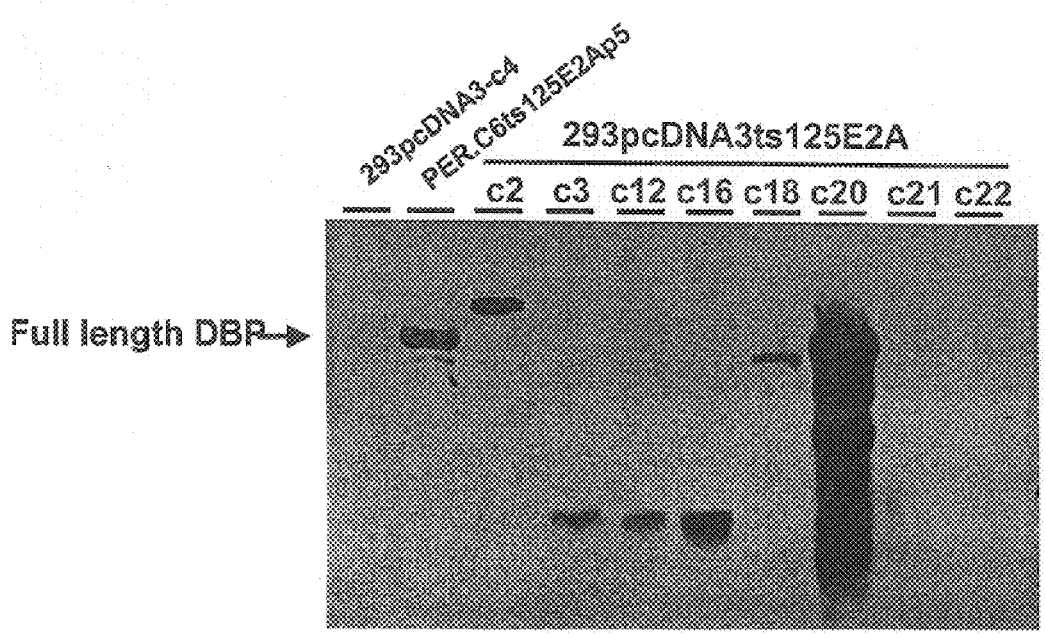
Figure 3: DBP expression in pcDNA3ts125E2A transfected 293 cells

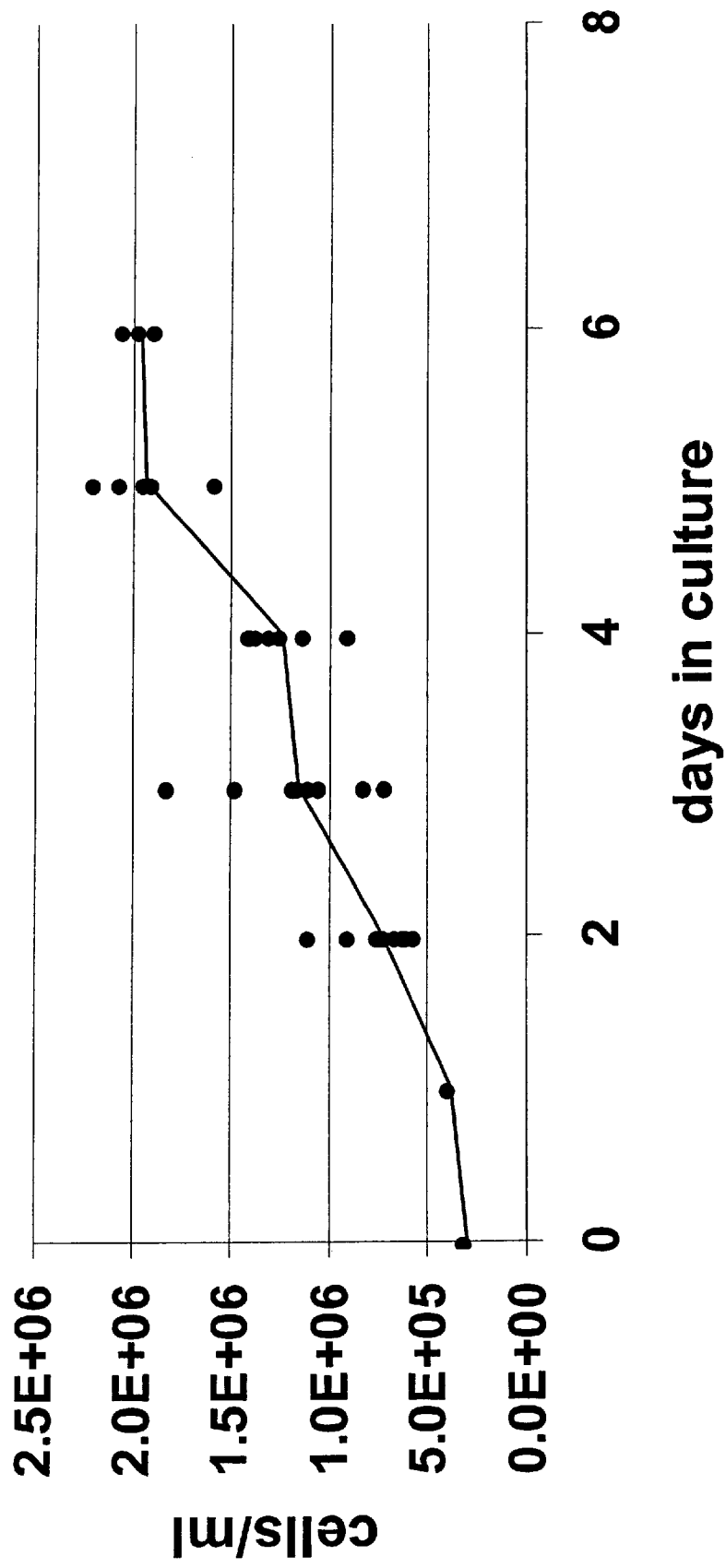
Figure 4: Suspension growth of PER.C6ts125E2A C5-9

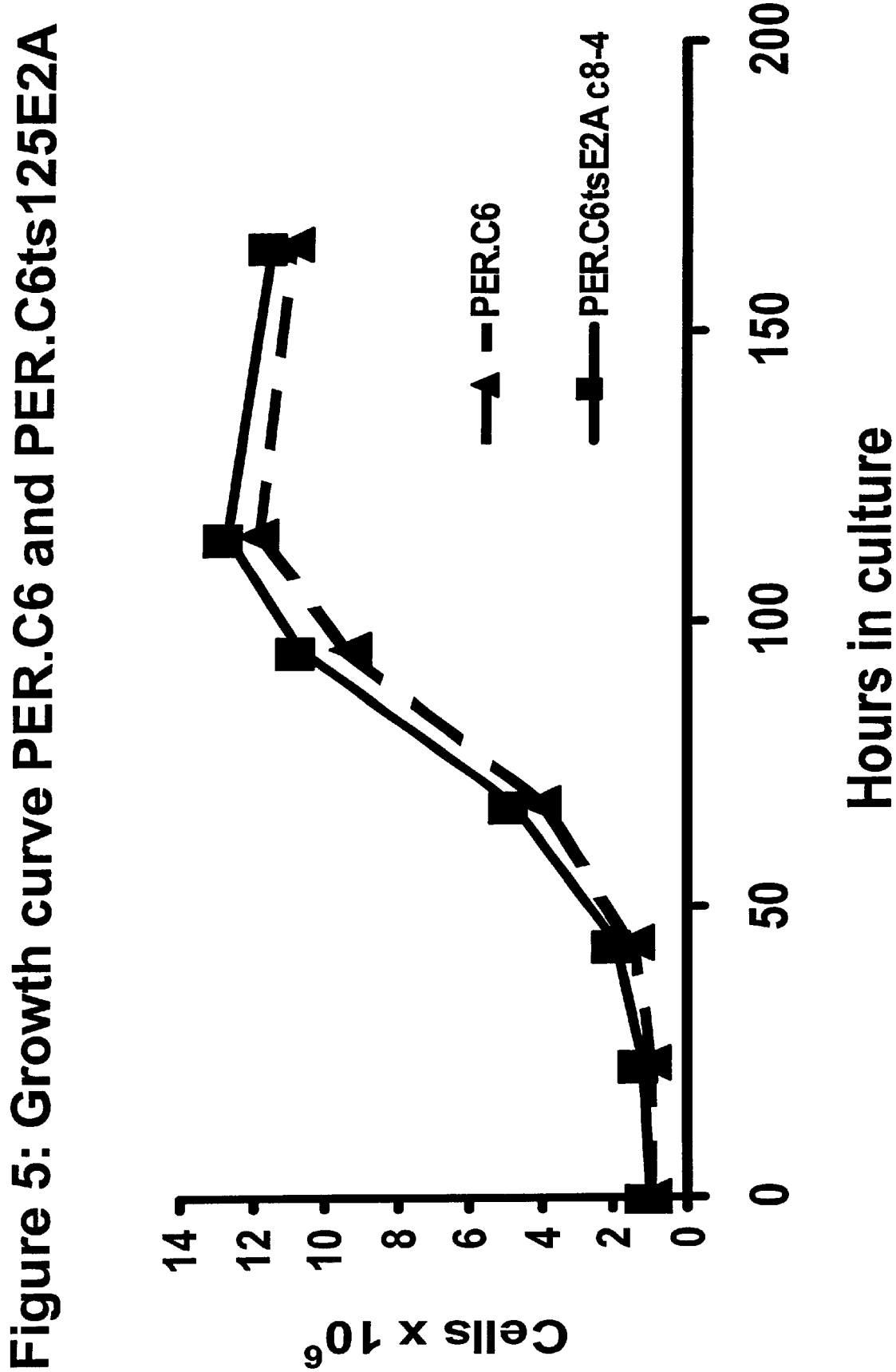

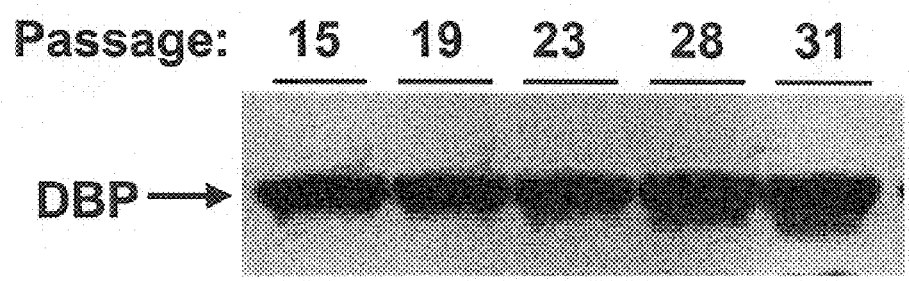
Figure 6: Stability of PER.C6ts125E2A

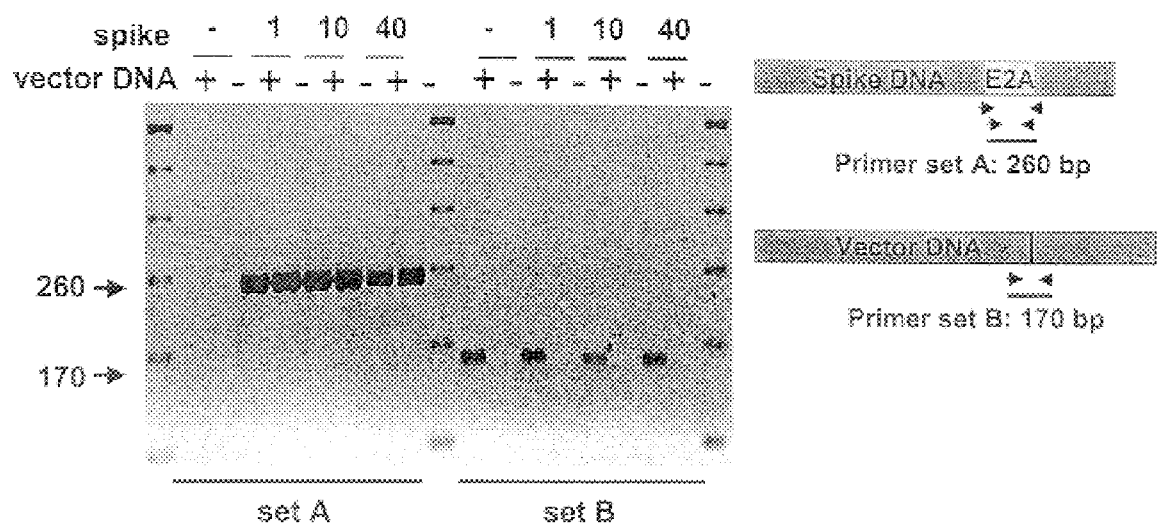
Figure 7: Revertant-Free manufacturing of ΔE1/E2A vectors

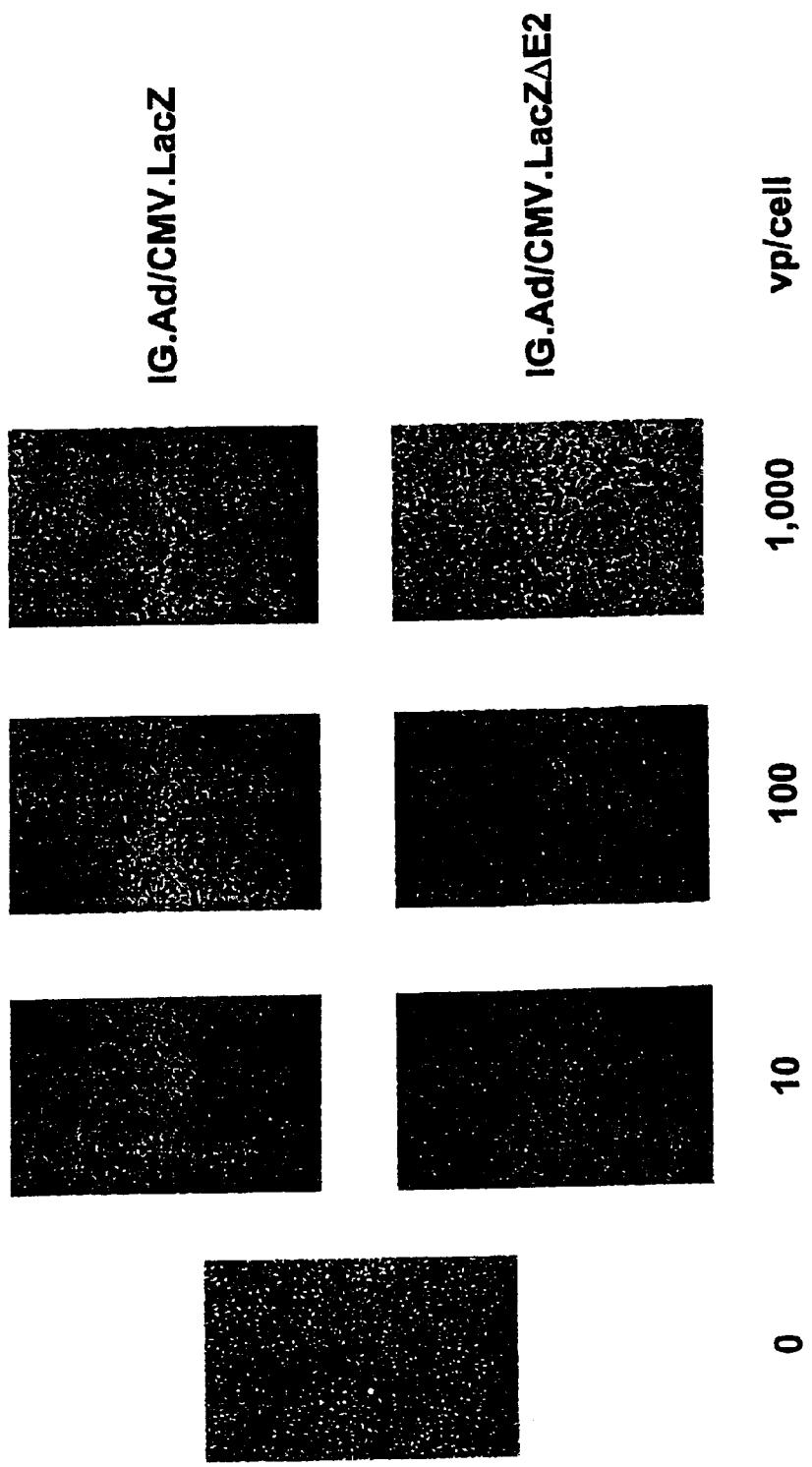
Figure 8: Transduction of Hela cells with IG.Ad/CMV.LacZ and IG.Ad/CMV.LacZΔE2A

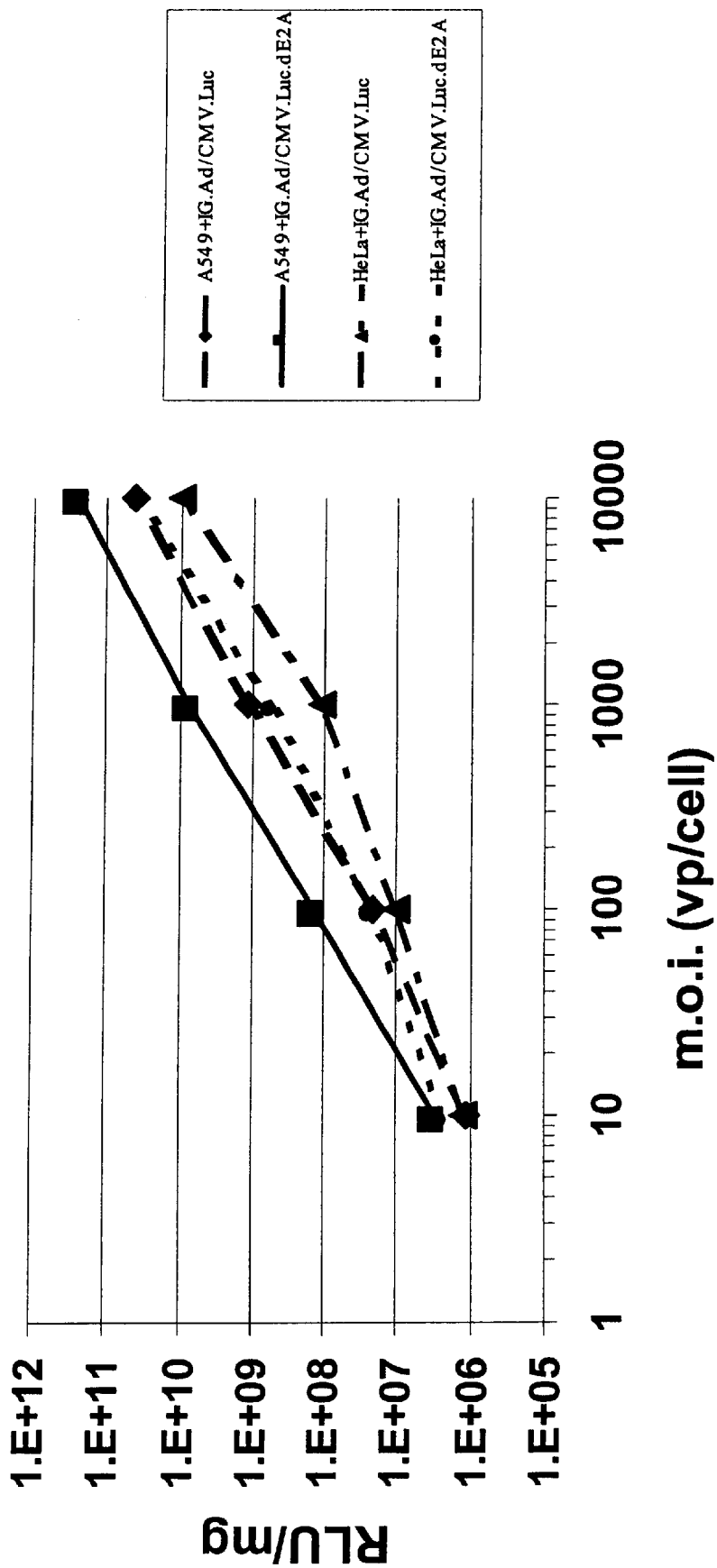
Figure 9: Luciferase activity in infected A549 and HeLa cells

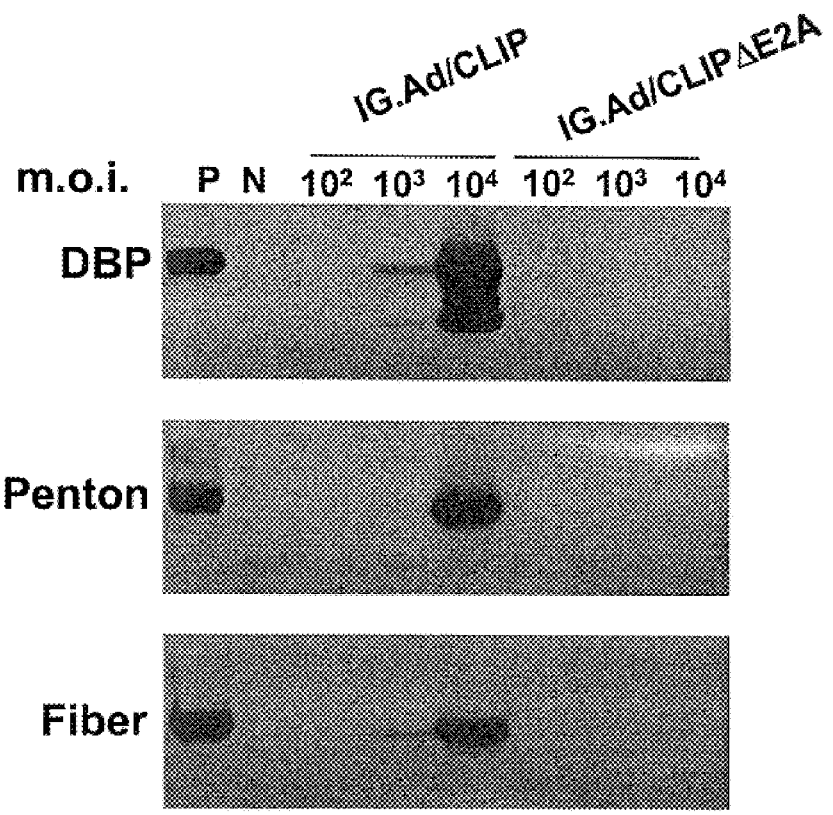
Figure 10: Expression of DBP, Penton and Fiber

MEANS AND METHODS FOR NUCLEIC ACID DELIVERY VEHICLE DESIGN AND NUCLEIC ACID TRANSFER

RELATED APPLICATIONS

This application is a continuation-in-part of U.S. patent application Ser. No. 08/793,170 filed Mar. 25, 1997, now U.S. Pat. No. 5,994,128 pending, incorporated herein by reference, which is the national stage filing of PCT/NL96/00244 filed Jun. 14, 1996, incorporated herein by reference, taking priority from EP 95201611.1 filed Jun. 15, 1995 and EP 95201728.3 filed Jun. 26, 1995, both of which are incorporated herein by reference.

TECHNICAL FIELD

The present invention relates to the field of recombinant DNA technology, more in particular to the field of gene therapy. Specifically, the present invention relates to gene therapy using materials derived from adenovirus, in particular human recombinant adenovirus, and relates to novel virus derived vectors and novel packaging cell lines for vectors based on adenoviruses. Furthermore, this invention also pertains to the screening of replication-competent and revertant E1 and/or E2A adenoviruses from recombinant adenoviruses used in gene therapy.

BACKGROUND

The current generation of adenoviral vectors for gene therapy contains deletions of the early region 1 ("E1"), where new genetic information can be introduced. The E1 deletion renders the recombinant virus replication defective. It was generally thought that E1-deleted vectors would not express any other adenoviral genes, because E1 is reported to trigger the transcription of the other adenoviral genes. It has been shown by us and others that these vectors express several early (e.g., E2A) and late genes (e.g., fiber and penton-base) in the absence of E1. This means that delivery of a therapeutic gene using E1-deleted adenoviral vectors will result in expression of the therapeutic protein and adenoviral proteins. A cytotoxic immune response is evoked against such transduced cells. It has been shown that cytotoxic T-lymphocytes ("CTLs") directed against both the transgene product and products encoded by the vector are activated, following vector administration into immunocompetent animals (Song et al., Hum. Gene Ther. 8: 1207, 1997; Yang et al., J. Virol. 70: 7209, 1996). Activated CTLs subsequently eradicate transduced cells from the recipient. Consistent with this, the longevity of transgene expression is significantly extended in immuno-deficient and immuno-compromised animals.

Expression of at least some adenoviral genes in a target cell is at least in part due to background replication of the recombinant adenoviral vector genome and/or background activity of promoters driving the respective adenoviral genes (Yang et al., Nature Genet. 7: 362, 1994; Lusky et al., J. Virol. 72: 2022, 1998). As a result of the expression of at least some adenovirus proteins in a target cell in a recipient, an immune response may be mounted against transduced cells. Such an immune response is often not desired, especially when long-term expression of a transgene is aimed for. One mechanism by which adenovirus proteins in a target cell in a recipient may cause the immune system of the recipient to remove the target cell is the following. Proteins encoded by expressed adenovirus genes can be processed into small peptides in a proteosome of the target cell. Peptides produced during this processing can subsequently be presented at the cell surface of the transduced cells in the complex of MHC class-I and βb2-microglobulin molecules. Finally, one or more of the peptides may be recognized as non-self peptides by circulating CTLs whereupon transduced cells can be eradicated from the recipient (reviewed in Ploegh, Science 280: 248, 1998).

DESCRIPTION OF THE INVENTION

In one aspect the present invention provides at least in part a solution to the problem of undesired removal of target cells in a recipient.

The present invention also provides, at least in part, a solution for the immune response against viral proteins. To this end, the invention provides improved recombinant adenoviral vectors that, in addition to deletion of E1, are also deleted for the adenoviral early 2A gene ("E2A gene" or "E2A"). The protein encoded by E2A is expressed from recombinant E1-deleted adenoviral vectors. In addition to that, residual expression of E2A from E1-deleted recombinant adenoviral vectors induces the expression of the viral late genes, since DNA binding protein ("DBP") has a positive regulatory effect on the adenovirus major late promoter ("MLP") and, therefore, on the expression of the late genes (Chang et al., J. Virol. 64: 2103, 1990). Deletion of the E2A gene from the recombinant adenoviral genome will therefore improve the characteristics of recombinant adenoviral vectors. First, deletion of E2A will eliminate the synthesis of DBP. Second, it will inhibit the background replication of the recombinant adenoviral backbone. Third, it will reduce the residual expression of the late genes. Finally, it will increase the capacity of the vector to harbor larger and/or multiple transgenes.

The E2A gene encodes the 72-kDa protein single stranded DBP whose activity is pivotal for the adenovirus DNA replication (reviewed in *The Molecular Repertoire of Adenoviruses II*, Springer-Verlag 1995). Therefore, manufacturing of vectors that are deleted for E2A requires a cell line that complements for the deletion of E2A in the recombinant adenoviral vector. Major hurdles in this approach are:

a) that E2A should be expressed to very high levels and b) that constitutive expression of E2A is toxic for cells and, therefore, impossible to achieve (Kiessig et al., Mol. Cell Biol. 4: 1354, 1984).

The current invention, therefore, involves the use of a temperature sensitive mutant of E2A derived from a temperature sensitive adenovirus under control of strong viral enhancer sequences, e.g., the cytomegalovirus enhancer for the generation of E2A complementing cell lines. DBP (ts125E2A) from hAd5ts125 is inactive at 39° C., but is fully active at 32° C. High levels of this protein can be maintained in the new complementing cells of the invention at the non-permissive temperature, until the switch is made to the permissive temperature. The invention also provides means and methods to use the complementing cell line, comprising E2A, tsE2A, or both E1 and tsE2A, for the generation of E2A- or E1- and E2A-deleted adenoviral vectors. The invention also involves inducible expression of E2A or tsE2A.

The invention also provides new cell lines that complement for E2A or for both the E1 and the E2A deletion in the vector. The invention also provides new recombinant adenoviral vectors deleted for E2A or both E1 and E2A.

BRIEF DESCRIPTION OF THE FIGURES

FIG. 1 depicts the temperature dependent growth of PER.C6. PER.C6 cells were cultured in Dulbecco's Modified Eagle Medium supplemented with 10% Fetal Bovine Serum (FBS, Gibco BRL) and 10 mM $MgCl_2$ in a 10% $CO_2$ atmosphere at either 32° C., 37° C. or 39° C. At day 0, a total of $1\times10^6$ PER.C6 cells were seeded per 25 cm² tissue culture flask (Nunc) and the cells were cultured at either 32° C., 37° C. or 39° C. At each of days 1–8, cells were counted. The growth rate and the final cell density of the PER.C6 culture at 39° C. are comparable to that at 37° C. The growth rate and final density of the PER.C6 culture at 32° C. were slightly reduced as compared to that at 37° C. or 39° C.

FIG. 2 depicts DBP levels in PER.C6 cells transfected with pcDNA3, pcDNA3wtE2A or pcDNA3ts125E2A. Equal amounts of whole-cell extract were fractionated by SDS-PAGE on 10% gels. Proteins were transferred onto Immobilon-P membranes and DBP protein was visualized using the aDBP monoclonal B6 in an ECL detection system. All of the cell lines derived from the pcDNA3ts125E2A transfecfion express the 72-kDa E2A-encoded DBP protein (left panel, lanes 4–14; middle panel, lanes 1–13; right panel, lanes 1–12). In contrast, the only cell line derived from the pcDNAwtE2A transfection did not express the DBP protein (left panel, lane 2). No DBP protein was detected in extract from a cell line derived from the pcDNA3 transfection (left panel, lane 1), which serves as a negative control. Extract from PER.C6 cells transiently transfected with pcDNA3ts125 (left panel, lane 3) served as a positive control for the Western blot procedure. These data confirm that constitutive expression of wtE2A is toxic for cells and that using the ts125 mutant of E2A can circumvent this toxicity.

FIG. 3 depicts DBP expression in pcDNA3ts125E2A transfected 293 cells. Equal amounts of whole-cell extract were fractionated by SDS-PAGE on 10% gels. Proteins were transferred onto Immobilon-P membranes and DBP protein was visualized using the aDBP monoclonal B6 in an ECL detection system. Clone 20 (lane 8) from the pcDNA3ts125E2A transfected 293 cells expressed the full-length ts125E2A encoded 72-kDa DBP. No E2A encoded DBP was detected in the extract from a cell line (clone 4) derived from the pcDNA3 transfected 293 cells (lane 1), which serves as a negative control. Extract from PER.C6 cells stably expressing ts125E2A encoded DBP (polyclonal cell line 5) (lane 2) served as a positive control for the Western blot procedure. The other 293 clones either did not express ts125E2A encoded DBP (clones 21 and 22, lanes 9 and 10 respectively) or expressed aberrant products running with a faster (clones 3, 12, 16 and 18, lanes 4–7) or slower (clone 2, lane 3) mobility in SDS/PAGE.

FIG. 4 depicts suspension growth of PER.C6ts125E2A cell line c5-9. PER.C6ts125E2Ac5-9 cells were seeded in a 125 ml tissue culture Erlenmeyer at a seeding density of $3\times10^5$ cells per ml in a total volume of 20 ml serum-free medium. Cells were furter cultured at 125 RPM on an orbital shaker at 39° C. in a 10% $CO_2$ atmosphere. Cells were counted at each of days 1–6. The mean growth curve from 8 cultures is shown. PER.C6ts125E2Ac5-9 performs well in serum-free suspension culture. The maximum cell density of approximately $2\times10^6$ cells per ml is reached within 5 days of culture.

FIG. 5 depicts growth curve PER.C6 and PER.C6tsE2A. PER.C6 cells or PER.C6ts125E2A (c8-4) cells were cultured at 37° C. or 39° C., respectively. At day 0, a total of $1\times10^6$ cells was seeded per 25 cm² tissue culture flask. At the indicated time points, cells were counted. The growth of PER.C6 cells at 37° C. is comparable to the growth of PER.C6ts125E2A c8-4 at 39° C. This shows that constitutive overexpression of ts125E2A has no adverse effect on the growth of cells at the non-permissive temperature of 39° C.

FIG. 6 depicts stability of PER.C6ts125E2A. For several passages, the PER.C6ts125E2A cell line clone 8-4 was cultured at 39° C. in medium without G418. Equal amounts of whole-cell extract from different passage numbers were fractionated by SDS-PAGE on 10% gels. Proteins were transferred onto Immobilon-P membranes and DBP protein was visualized using the aDBP monoclonal B6 in an ECL detection system. The expression of ts125E2A encoded DBP is stable for at least 16 passages, which is equivalent to approximately 40 cell doublings. No decrease in DBP levels was observed during this culture period, indicating that the expression of ts125E2A is stable, even in the absence of G418 selection pressure.

FIG. 7 depicts revertant-free manufacturing of DE1/E2A vectors. The recombinant adenoviral vector DNA was screened for reversion of the E2A deleted phenotype by PCR. As shown in the left panel, E2A sequences were amplified from the DNA samples (+) and control samples (−) spiked with both 1, 10 and 40 molecules using primer set A, as evidenced by the amplification of a 260 base pair ("bp") DNA fragment. In contrast, no E2A sequences were amplified from the non-spiked samples, showing that reversion of the E2A-deleted did not occur. As shown in the right panel, the PCR reactions with primer set B yielded the expected DNA fragment of 169 bp in the samples containing the recombinant adenoviral vector DNA (+). From the negative control samples containing the water instead of DNA (−), no DNA fragment of 169 bp was amplified. These data show that elimination of overlap between adenoviral sequences in the vector and cell line prevents reversion of the E2A-deleted phenotype.

FIG. 8 depicts transduction of HeLa cells with IG.Ad/CMV.LacZ and IG.Ad/CMV.LacZDE2A. HeLa cells were infected with a multiplicity of infection ("m.o.i.") of either 0, 10, 100 or 1000 viral particles IG.Ad/CMV.LacZ or IG.Ad/CMV.LacZDE2A per cell. Forty-eight hours post infection, cells were stained with X-gal solution. IG.Ad/CMV.LacZDE2A transduced HeLa cells stained at least as good as did IG.Ad/CMV.LacZ, at all m.o.i.'s.

FIG. 9 depicts luciferase activity in infected A549 and HeLa cells. HeLa and A549 cells were infected with a m.o.i. of either 0, 10, 100, 1,000 or 10,000 virus particles ("vp") IG.Ad/CLIP.Luc or IG.Ad/CLIP.LucDE2A per cell. Two days post infection, cells were lysed and the luciferase activity was determined. Both the IG.Ad/CLIP.LucDE2A infected HeLa and A549 cells produce more luciferase enzyme than the IG.Ad/CLIP.Luc infected HeLa and A549 and HeLa cells, at all m.o.i.'s tested.

FIG. 10 depicts the expression of DBP, Penton and Fiber. A549 cells were infected with a m.o.i. of either 0, 100, 1,000 or 10,000 vp/cell IG.Ad/CLIP or IG.Ad.CLIPDE2A. Seventy-two hours post infection, cell extracts were prepared and equal amounts of whole cell extract were fractionated by SDS-PAGE on 10% gels. The proteins were visualized with the aDBP monoclonal B6, the polyclonal a-Penton base Ad2-Pb571 or the polyclonal a-knob domain of fiber E641/3, using an ECL detection system. Cells infected with IG.Ad.CLIP express both E2A encoded DBP, Penton base and Fiber proteins. The proteins co-migrate with the respective proteins in the positive control (lane P, extract from PER.C6 cells infected with IG.Ad.CLIP harvested at starting CPE). In contrast, no DBP, penton-base or fiber was detected in the non-infected A549 cells or cells infected with IG.Ad.CLIPDE2A. These data show that deletion of the E2A gene did not only eliminate residual DBP expression, but also the residual expression of the late adenoviral proteins penton-base and fiber.

BEST MODE OF THE INVENTION

According to a presently preferred embodiment of the invention, a cell according to the invention is capable of at least, in part, complementing adenovirus E2A function of an adenovirus defective in E2A function. Such a cell includes a nucleic acid encoding adenovirus E2A or a functional part, derivative and/or analogue thereof, integrated into the genome of the cell. Preferably, the cell has E2A nucleic acid derived from a temperature sensitive adenovirus such as but not limited to adenovirus ts125. More preferably, such a cell further includes a nucleic acid encoding adenovirus E1-region proteins or a fuinctional part, derivative and/or analogue thereof Such a cell could be derived from the "PER.C6" cell line (commercially available from IntroGene, by, and deposited, under ECACC deposit accession number 96022940 under the provisions of the Budapest Treaty with the Centre for Applied Microbiology and Research Authority (European Collection of Animal Cell Cultures), Porton Down, Salisbury, Wiltshire SP4, OJG, United Kingdom, an International Depository Authority, in accordance with the Budapest Treaty, on Feb. 29, 1996.

The invention also includes a method for producing an adenovirus particle containing an adenovirus vector with a functional deletion of E2A. Such a method involves providing a cell as previously described with the finctionally deleted adenovirus vector, culturing the cell, and harvesting the virus particle. In such a method, the functional deletion can comprise a deletion of at least part of the nucleic acid encoding E2A. In such a method, the nucleic acid encoding adenovirus E2A in the genome of the cell preferably has no sequence overlap with the vector which leads to replication competent adenovirus and/or to the formation of an adenovirus vector comprising E2A function. In the method, the adenovirus vector preferably further comprises a functional deletion of E1-region encoding nucleic acid, comprising providing one of the previously described cells with the adenovirus vector, culturing the cell and harvesting the virus particle. In such a method, the nucleic acid encoding adenovirus E1-region preferably does not comprise sequence overlap with the vector which leads to replication competent adenovirus and/or to the formation of an adenovirus vector comprising an E1 function. Furthermore, in the method, the adenovirus vector further comprises at least one nucleic acid of interest.

The invention also includes an adenovirus vector comprising a functional deletion of adenovirus E2A. Such a functional deletion is preferably a deletion of at least part of the nucleic acid encoding E2A. The deletion may encompass the entire coding region of E2A. Such an adenovirus vector preferably includes a deletion corresponding to a deletion of nucleotides 22443 to 24032 in adenovirus 5. The deletion can include a deletion of nucleic acid encoding E1-region proteins. The deletion of nucleic acid encoding E1-region proteins can comprise a deletion corresponding to a deletion of nucleotides 459 to 3510 in adenovirus 5. Again, the adenovirus vector preferably further includes at least one nucleic acid of interest.

An adenovirus vector according to the invention can, but does not necessarily, also comprise at least a deletion of a region which ini adenovirus 5 corresponds to nucleotides 22418–24037 or a deletion of a region which in adenovirus 5 corresponds to nucleotides 22443–24032. Such vectors can further comprise at least nucleic acid which in adenovirus 5 corresponds to nueotides 3534–22347 and/or nucleotides 24060 until the right ITR or at least 3534–22417 and/or 24038 until the right ITR or at least nucleic acid which in adenovirus 5 corresponds to nucleotides 3534–22442 and/or nucleotides 24033 until the right ITR.

The invention also includes preparations of adenovirus vector containing adenoviws particles wherein the adenovirus vector comprises a functional deletion of E2A. Such an adenovirus vectorpreferably further includes a deletion of nucleic acid encoding E1-region proteins, and may be free of adenovirus vectors comprising E2A function. In such a case the preparation may be free of adenovirus vectors comprising nucleic acid encoding a functional E2A, or a functional part, derivative and/or analogue thereof. The preparation is preferably free of adenovirus vectors comprising nucleic acid encoding E1-region proteins or parts, derivatives and/or analogues thereof.

The invention also includes a method for providing cells of an individual with a nucleic acid of interest, without risk of administering simultaneously a replication competent adenovirus vector, comprising administering the individual one of the previously described preparations.

The invention is furter described by the use of the following illustrative Examples.

EXAMPLE I

Generation of Producer Cell Lines for the Production of Recombinant Adenoviral Vectors Deleted in E1 and E2A or E1 and E2A Here is described the generation of cell lines for the production of recombinant adenoviral vectors that are deleted in E1 and E2A. The producer cell lines complement for the E1 and E2A deletion from recombinant adenoviral vectors in trans by constitutive expression of the E1 and E2A genes, respectively. The pre-established Ad5-E1 transformed human embryo retinoblast cell line PER.C6 (commercially avallable from IntroGene, bv of Leiden, NL, see also International Patent Appln. WO 97/00326) and Ad5 transformed human embryo kidney cell line 293 (Graham et al., *J. Gen. Virol.* 36: 59, 1977) were further equipped with E2A expression cassettes.

The adenoviral E2A gene encodes a 72 kDa DBP which has a high affinity for single stranded DNA. Because of its function, constitutive expression of DBP is toxic for cells. The ts125E2A mutant encodes a DBP which has a Pro-→Ser substitution of amino acid 413 (van der Vliet, *J. Virol.* 15: 348, 1975). Due to this mutation, the ts125E2A encoded DBP is fully active at the permissive temperature of 32° C., but does not bind to ssDNA at the non-permissive temperature of 39° C. This allows the generation of cell lines that constitutively express E2A, which is not functional and is not toxic at the non-permissive temperature of 39° C. Temperature sensitive E2A gradually becomes functional upon temperature decrease and becomes fully functional at a temperature of 32° C., the permissive temperature.

A. Generation of Plasmids Expressing the Wild Type E2A- or Temperature Sensitive ts125E2A Gene.

pcDNA3wtE2A: The complete wild-type E2A coding region was amplified from the plasmid pBR/Ad.Bam-rITR (ECACC deposit P97082122) with the primers DBPpcr1 and DBPpcr2 using the Expand™ Long Template PCR system according to the standard protocol of the supplier (Boehringer Mannheim). The PCR was performed on a Biometra TRIO THERMOBLOCK, using the following amplification program: 94° C. for 2 minutes, 1 cycle; 94° C. for 10 seconds +51° C. for 30 seconds +68° C. for 2 minutes, 1 cycle; 94 ° C. for 10 seconds+58° C. for 30 seconds+68° C. for 2 minutes, 10 cycles ; 94° C. for 10 seconds+58° C.

for 30 seconds+68° C. for 2 minutes with 10 seconds extension per cycle, 20 cycles; 68° C. for 5 minutes, 1 cycle. The primer DBPpcr1: CG<u>G TA CC</u>G CCA CCA TGG CCA GTC GGG AAG AGG AG (5' to 3') (SEQ ID NO:1) contains a unique BamHI restriction site (underlined) 5' of the Kozak sequence (italic) and start codon of the E2A coding sequence. The primer DBPpcs2: CG<u>G AAT TCT</u> TAA AAA TCA AAG GGG TTC TGC CGC (5' to 3') (SEQ ID NO:2) contains a unique EcoRI restriction site (underlined) 3' of the stop codon of the E2A coding sequence. The bold characters refer to sequences derived from the E2A coding region. The PCR fragment was digested with BamHI/EcoRI and cloned into BamHI/EcoRI digested pcDNA3 (Invitrogen), giving rise to pcDNA3wtE2A.

pcDNA3tsE2A: The complete ts125E2A-coding region was amplified from DNA isolated from the temperature sensitive adenovirus mutant H5ts125 (Ensinger et al., J. Virol. 10: 328, 1972; van der Vliet et al., *J. Virol.* 15: 348, 1975). The PCR amplification procedure was identical to that for the amplification of wtE2A. The PCR fragment was digested with BamHI/EcoRI and cloned into BamHI/EcoRI digested pcDNA3 (Invitrogen), giving rise to pcDNA3tsE2A. The integrity of the coding sequence of wtE2A and tsE2A was confirmed by sequencing.

B. Growth Characteristics of Producer Cells for the Production of Recombinant Adenoviral Vectors Cultured at 32°, 37° and 39° C.

PER.C6 cells were cultured in Dulbecco's Modified Eagle Medium ("DMEM", Gibco BRL) supplemented with 10% FBS and 10 mM MgCl$_2$ in a 10% CO$_2$ atmosphere at either 32° C., 37° C. or 39° C. At day 0, a total of 1×10$^6$ PER.C6 cells were seeded per 25 cm$^2$ tissue culture flask (Nunc) and the cells were cultured at either 32° C., 37° C. or 39° C. At each of days 1–8, cells were counted. FIG. 1 shows that the growth rate and the final cell density of the PER.C6 culture at 39° C. are comparable to that at 37° C. The growth rate and final density of the PER.C6 culture at 32° C. were slightly reduced as compared to that at 37° C. or 39° C. No significant cell death was observed at any of the incubation temperatures. Thus PER.C6 performs very well both at 32° C. and 39° C., the permissive and non-permissive temperature for ts125E2A, respectively.

C. Transfection of PBR.C6 and 293 with E2A Expression Vectors; Colony Formation and Generation of Cell Lines One day prior to transfection, 2×10$^4$ PER.C6 cells were seeded per 6 cm tissue culture dish (Greiner) in DMEM, supplemented with 10% FBS and 10 mM MgCl$_2$ and incubated at 37° C. in a 10% CO$_2$ atmosphere. The next day, the cells were transfected with 3, 5 or 8 μg of either pcDNA3, pcDNA3wtE2A or pcDNA3tsE2A plasmid DNA per dish, using the LipofectAMINE PLUS™ Reagent Kit according to the standard protocol of the supplier (Gibco BRL), except that the cells were transfected at 39° C. in a 10% CO$_2$ atmosphere. After the transfection, the cells were constantly kept at 39° C., the non-permissive temperature for ts125E2A. Three days later, the cells were put on DMEM, supplemented with 10% FBS, 10 mM MgCl$_2$ and 0.25 mg/ml G418 (Gibco BRL) and the first G418 resistant colonies appeared at 10 days post transfection. As shown in Table 1, there was a dramatic difference between the total number of colonies obtained after transfection of pcDNA3 (~200 colonies) or pcDNA3tsE2A (~100 colonies) and pcDNA3wtE2A (only 4 colonies). These results indicate that the constitutive expression of E2A is toxic and the toxicity of constitutively expressed E2A can be overcome by using a temperature sensitive mutant of E2A (ts125E2A) and culturing of the cells at the non-permissive temperature of 39° C.

TABLE 1

Number of colonies after transfection of PER.C6 with E2A expression vectors

| plasmid | number of colonies | cell lines established |
|---|---|---|
| pcDNA3 | ~200 | 4/4 |
| PcDNA3wtE2A | 4 | 1/4 |
| PcDNA3tsE2A | ~100 | 37/45 |

PER.C6 cells were transfected with either pcDNA3, pcDNA3wtE2A or pcDNA3wtE2A and cultured in selection medium containing 0.25 mg/ml G418 at 39° C. All colonies (4/4) picked from the pcDNA3 transfection and 82% (37/45) of the colonies from the pcDNA3tsE2A transfection were established to stable cell lines. In contrast, only 25% (1/4) of the colonies from the pcDNA3wtE2A transfection could be established to a cell line.

From each transfection, a number of colonies was picked by scraping the cells from the dish with a pipette. The detached cells were subsequently put into 24 well tissue culture dishes (Greiner) and cultured further at 39° C. in a 10% CO$_2$ atmosphere in DMEM, supplemented with 10% FBS, 10 M MgCl$_2$ and 0.25 mg/ml G418. As shown in Table 1, 100% of the pcDNA3 transfected colonies (4/4) and 82% of the pcDNA3tsE2A transfected colonies (37/45) were established to stable cell lines (the remaining 8 pcDNA3tsE2A transfected colonies grew slowly and were discarded). In contrast, only 1 pcDNA3wtE2A-transfected colony could be established. The other 3 died directly after picking.

Next, the E2A expression levels in the different cell lines were determined by Western blotting. The cell lines were seeded on 6 well tissue culture dishes and subconfluent cultures were washed twice with PBS (NPBI) and lysed and scraped in RIPA (1% NP-40, 0.5% sodium deoxycholate and 0.1% SDS in PBS, supplemented with 1 mM phenylmethylsulfonylfluoride and 0.1 mg/ml trypsin inhibitor). After 15 minutes incubation on ice, the lysates were cleared by centrifuigation. Protein concentrations were determined by the Bio-Rad protein assay, according to standard procedures of the supplier (BioRad). Equal amounts of whole-cell extract were fractionated by SDS-PAGE on 10% gels. Proteins were transferred onto Immobilon-P membranes (Millipore) and incubated with the αDBP monoclonal antibody B6 (Reich et al., Virology 128: 480, 1983). The secondary antibody was a horseradish-peroxidase-conjugated goat anti mouse antibody (BioRad). The Western blotting procedure and incubations were performed according to the protocol provided by Millipore. The complexes were visualized with the ECL detection system according to the manufacturer's protocol (Amersham). FIG. 2 shows that all of the cell lines derived from the pcDNA3tsE2A transfection express the 72-kDa E2A protein (left panel, lanes 4–14; middle panel, lanes 1–13; right panel, lanes 1–12). In contrast, the only cell line derived from the pcDNAwtE2A transfection did not express the E2A protein (left panel, lane 2). No E2A protein was detected in extract from a cell line derived from the pcDNA3 transfection (left panel, lane 1), which serves as a negative control. Extract from PER.C6 cells transiently transfected with pcDNA3ts125 (leftpanel, lane 3) served as a positive control for the Western blot procedure. These data confirm that constitutive expression of wtE2A is toxic for cells and that using the ts125 mutant of E2A can circumvent this toxicity.

In contrast to PER.C6 cells, the culturing of 293 cells at 39° C. is troublesome. Therefore, the transfection of 293 cells with either pcDNA3, pcDNA3wtE2A or pcDNA3tsE2A was performed at 37° C. in an atmosphere of 10% $CO_2$, a semi-permissive temperature for ts125E2A encoded DBP. A day prior to transfection, 293 cells were seeded in DMEM, supplemented with 10% FBS and 10 mM $MgCl_2$, at a density of $3.6 \times 10^5$ cells per 6 cm tissue culture dish (Greiner). Five hours before transfection, cells received fresh medium. Cells were transfected with 7.2 µg of either pcDNA3, pcDNA3wtE2A or pcDNA3tsE2A plasmid DNA using the Calcium Phosphate Transfection System according to the standard protocol of the supplier (Gibco BRL). Two days post transfection, cells were put on selection medium, i.e., DMEM supplemented with 10% FBS, 10 mM $MgCl_2$ and 0.1 mg/ml G418. The first colonies appeared at day 12 post transfection. As shown in Table 2, the total number of colonies obtained after transfection of pcDNA3 (~100 colonies) or pcDNA3tsE2A (~25 colonies) was significantly higher than that obtained after transfection of pcDNA3wtE2A (only 2 colonies). A total of 22 clones from the pcDNA3tsE2A transfection were picked by scraping the cells from the dish with a pipette. The detached cells were subsequently put into 96 well tissue culture dishes (Greiner) and cultured further at 37° C. in a 10% $CO_2$ atmosphere in DMEM, supplemented with 10% FBS, 10 mM $MgCl_2$ and 0.1 mg/ml G418. sixteen out of the 22 picked colonies could be established as cell lines (the 6 remaining colonies grew badly and were discarded).

TABLE 2

Number of colonies after transfection of 293 with E2A expression vectors

| plasmid | number of colonies |
| --- | --- |
| pcDNA3 | ~100 |
| PcDNA3wtE2A | 2 |
| PcDNA3tsE2A | 25 |

Selection of colonies derived from 293 cells transfected with E2A expression cassettes. Cell line 293 was transfected with either pcDNA3, pcDNA3wtE2A or pcDNA3wtE2A and cultured in selection medium containing 0.1 mg/ml G418 at 37° C.

Next, the E2A expression level in 8 different cell lines was determined by Western blotting. The cell lines were seeded on 6 well tissue culture dishes and sub-confluent cultures were washed twice with PBS (NPBI) and lysed and scraped in RIPA (1% NP-40, 0.5% sodium deoxycholate and 0.1% SDS in PBS, supplemented with 1 mM phenylmethylsulfonylfluoride and 0.1 mg/ml trypsin inhibitor). After 15 minutes incubation on ice, the lysates were cleared by centrifugation. Protein concentrations were determined by the BioRad protein assay, according to standard procedures of the supplier (BioRad). Equal amounts of wholecell extract were fractionated by SDS-PAGE on 10% gels. Proteins were transferred onto Immobilon-P membranes (Millipore) and incubated with the αDBP monoclonal antibody B6 (Reich et al., Virology 128: 480, 1983). The secondary antibody was a horseradish-peroxidase-conjugated goat anti mouse antibody (BioRad). The Western blotting procedure and incubations were performed according to the protocol provided by Millipore. The complexes were visualized with the ECL detection system according to the manufacturer's protocol (Amersham). FIG. 3 shows, that, in contrast to the PER.C6tsE2A cell lines, only clone 20 (lane 8) from the pcDNA3tsE2A transfected 293 cells expressed the full-length ts125E2A encoded 72-kDa DBP. No E2A encoded DBP was detected in extract from a cell line (clone 4) derived from the pcDNA3 transfected 293 cells (lane 1), which serves as a negative control. Extract from PER.C6 cells stably expressing ts125E2A encoded DBP (polyclonal cell line 5) (lane 2) served as a positive control for the Western blot procedure. The other 293 clones either did not express ts125E2A encoded DBP (clones 21 and 22, lanes 9 and 10 respectively) or expressed aberrant products running with a faster (clones 3, 12, 16 and 18 lanes 4–7) or slower (clone 2, lane 3) mobility in SDS/PAGE. These results show that generation of E2A complementing cell line by using temperature sensitive mutants of E2A is not specific for PER.C6 cells, but that it applies to eukaryotic cells in general (e.g., 293 cells). In addition, the 293 data show that keeping the temperature sensitive E2A encoded DBP as inactive as possible is crucial for easy generation of such cell lines. The 293 cell lines were generated at an intermediate temperature of 37° C., a temperature at which ts125E2A encoded DBP is only partially inactivated. This explains the high number of cell lines expressing aberrant DBP products.

D. Complementation of E2A Deletion in Adenoviral Vectors on PER.C6- and 293 Cells Constitutively Expressing Full-length ts125E2A Encoded DBP.

The adenovirus Ad5.d1802 is an Ad 5 derived vector deleted for the major part of the E2A coding region and does not produce functional DBP (Rice et al., J. Virol. 56: 767, 1985). Ad5.d1802 was used to test the E2A transcomplementing activity of PER.C6 cells constitutively expressing ts125E2A. Parental PER.C6 cells or PER.C6tsE2A clone 3–9 were cultured in DMEM, supplemented with 10% FBS and 10 mM $MgCl_2$ at 39° C. and 10% $CO_2$ in 25 $cm^2$ flasks and either mock infected or infected with Ad5.d1802 at an m.o.i. of 5. Subsequently, the infected cells were cultured at 32° C. and cells were screened for the appearance of a cytopathic effect (CPE) as determined by changes in cell morphology and detachment of the cells from the flask. Table 3 shows that full CPE appeared in the Ad5.d1802 infected PER.C6tsE2A clone 3–9 within 2 days. No CPE appeared in the Ad5.d1802 infected PER.C6 cells or the mock infected cells. These data show that PER.C6 cells constitutively expressing ts125E2A complement in trans for the E2A deletion in the Ad5.d1802 vector at the permissive temperature of 32° C.

These cells are therefore suitable for production of recombinant adenoviral vector that are deficient for functional E2A.

TABLE 3

Complementation of E2A deletion in adenoviral vectors on PER.C6 cells and PER.C6 cells constitutively expressing temperature sensitive E2A

|  | 32° C. day 2 |
| --- | --- |
| PER.C6 mock | — |
| PER.C6 dl802 | — |
| PER.C6ts125c3–9 mock | — |
| PER.C6ts125c3–9 dl802 | Full CPE |

Parental PER.C6 cells or PER.C6ts125E2A clone 3–9 were infected with Ad5.dl802, an Ad5 adenovirus deleted for the E2A gene, at an m.o.i. of 5. Subsequently, the infected cells were cultured at 32° C. and cells were screened for the appearance of a cytopathic effect (CPE) as determined by changes in cell morphology and detachment of the cells from the flask.

The 293tsE2A clones c2, c16, c18 and c20 and the 293pcDNA3-clone c4 were tested for their E2A trans-complementing activity as follows. The cell lines were cultured in DMEM, supplemented with 10% FBS and 10 mM $MgCl_2$ at 39° C. and 10% $CO_2$ in 6 well plates and either mock infected or infected with IG.Ad.CLIP.Luc (see below) at an m.o.i. of 10. Subsequently, the infected cells were cultured at either 32° C. or 39° C. and cells were screened for the appearance of a cytopathic effect (CPE) 3 days post infection, as determined by changes in cell morphology and detachment of the cells from the flask. Table 4 shows that no CPE appeared in the control cell line 293 pcDNA3-c4. Moreover, the cell lines expressing aberrant forms of DBP either failed to complement this vector (clones 16 and 18) or were intermediate in the transcomplementing ability (clone 2). Only the 293 cell line expressing full-length ts125E2A encoded DBP (ie., clone 20) fully complemented for the E2A deletion in the vector IG.Ad.CLIP.Luc at the permissive temperature of 32° C. No CPE appeared at the non-permissive temperature of 39° C.

TABLE 4

Complementation of E2A deletion in adenoviral vectors on 293 cells and 293 cells constitutively expressing temperature sensitive E2A

| Cell line | CPE at 32° C. | CPE at 39° C. |
| --- | --- | --- |
| 293pcDNA3-c4 | – | – |
| 293ts125E2A-c2 | +/– | – |
| 293ts125E2A-c16 | – | – |
| 293ts125E2A-c18 | – | – |
| 293ts125E2A-c20 | + | – |

The 293ts125E2A clones c2, c16, c18 and c20 and the 293pcDNA3-clone c4 were tested for their E2A trans-complementing activity as follows. The cell lines were either mock infected or infected with IG.Ad.CLIP.Luc at an m.o.i. of 10. Subsequently, the infected cells were cultured at either 32° C. or 39° C. and cells were screened for the appearance of a cytopathic effect (CPE) 3 days post infection, as determined by changes in cell morphology and detachment of the cells from the flask.

E. Serum-free Suspension Culture of PER.C6tsE2A Cell Lines.

Large-scale production of recombinant adenoviral vectors for human gene therapy requires an easy and scalable culturing method for the producer cell line, preferably a suspension culture in medium devoid of any human or animal constituents. To that end, the cell line PER.C6tsE2A c5-9 (designated c5-9) was cultured at 39° C. and 10% $CO_2$ in a 175 $cm^2$ tissue culture flask (Nunc) in DMEM, supplemented with 10% FBS and 10 mM $MgCl_2$. At sub-confluency (70–80% confluent), the cells were washed with PBS (NPBI) and the medium was replaced by 25 ml serum free suspension medium Ex-cell™ 525 (JRH) supplemented with 1×L-Glutamin (Gibco BRL), hereafter designated SFM. Two days later, cells were detached from the flask by flicking and the cells were centrifuged at 1000 rpm for 5 minutes. The cell pellet was re-suspended in 5 ml SFM and 0.5 ml cell suspension was transferred to an 80 $cm^2$ tissue culture flask (Nunc), together with 12 ml fresh SFM. After 2 days, cells were harvested (all cells are in suspension) and counted in a Burker cell counter. Next, the cells were seeded in a 125 ml tissue culture Erlenmeyer (Corning) at a seeding density of $3\times10^5$ cells per ml in a total volume of 20 ml SFM. Cells were further cultured at 125 RPM on an orbital shaker (GFL) at 39° C. in a 10% $CO_2$ atmosphere. Cells were counted at day 1–6 in a Burker cell counter. In FIG. 4, the mean growth curve from 8 cultures is shown. PER.C6tsE2A c5-9 performs well in serumrfree suspension culture. The maximum cell density of approximately $2\times10^6$ cells per ml is reached within 5 days of culture.

F. Growtn Characteristics of PER.C6 and PER.C6/2A at 37° C. and 39° C.

PER.C6 cells or PER.C6ts125E2A (c8-4) cells were cultured in DMEM supplemented with 10% FBS and 10 mM $MgCl_2$ in a 10% $CO_2$ atmosphere at either 37° C. (PER.C6) or 39° C. (PER.C6ts125E2A c8-4). At day 0, a total of $1\times10^6$ cells were seeded per 25 $cm^2$ tissue culture flask (Nunc) and the cells were cultured at the respective temperatures. At the indicated time points, cells were counted. FIG. 5 shows that the growth of PER.C6 cells at 37° C. is comparable to the growth of PER.C6ts125E2A c8-4 at 39° C. This shows that constitutive expression of ts125E2A encoded DBP has no adverse effect on the growth of cells at the non-permissive temperature of 39° C.

G. Stability of PER.C6ts125E2A

For several passages, the PER.C6ts125E2A cell line clone 8-4 was cultured at 39° C. and 10% $CO_2$ in a 25 $cm^2$ tissue culture flask (Nunc) in DMEM, supplemented with 10% FBS and 10 mM $MgCl_2$ in the absence of selection pressure (G418). At sub-confluency (70–80% confluent), the cells werewashed with PBS (NPBI) and lysed and scraped in RIPA (1% NP-40, 0.5% sodium deoxycholate and 0.1% SDS in PBS, supplemented with 1 nmM phenylmethylsulfonylfluoride and 0.1 mg/ml trypsin inhibitor). After 15 minutes incubation on ice, the lysates were cleared by centrifugation. Protein concentrations were determined by the BioRad protein assay, according to standard procedures of the supplier (BioRad). Equal amounts of whole-cell extract were fractionated by SDS-PAGE on 10% gels. Proteins were transferred onto Immobilon-P membranes (Millipore) and incubated with the aDBP monoclonal antibody B6 (Reich et al., *Virology* 128: 480, 1983). The secondary antibody was a horseradish-peroxidase-conjugated goat anti mouse antibody (BioRad). The Western blotting procedure and incubations were performed according to the protocol provided by Millipore. The complexes were visualized with the ECL detection system according to the manufacturer's protocol (Amersham). FIG. 6 shows that the expression of ts125E2A encoded DBP is stable for at least 16 passages, which is equivalent to approximately 40 cell doublings. No decrease in DBP levels was observed during this culture period, indicating that the expression of ts125SE2A is stable, even in the absence of G418 selection pressure.

EXAMPLE II

Plasmid Based System for the Generation of Recombinant Adenoviral Vectors Deleted in E1 and E2A A. Generation of pBr/Ad.Bam-rITR (ECACC deposit P97082122)

In order to facilitate blunt end cloning of the inverted terminal repeat ("ITR") sequences, wild-type human adenovirus type 5 (Ad5) DNA was treated with Klenow enzyme in the presence of excess dNTPs. After inactivation of the Kienow enzyme and purification by phenol/chloroform extraction followed by ethanol precipitation, the DNA was digested with BamHI. This DNA preparation was used without further purification in a ligation reaction with pBr322 derived vector DNA prepared as follows: pBr322 DNA was digested with EcoRV and BamHI, de-phosphorylated by treatment with TSAP enzyme (Life Technologies) and purified on LMP agarose gel (SeaPlaque GTG). After transformation into competent *E.coli* DH5a (Life Techn.) and analysis of ampicillin resistant colonies, one clone was selected that showed a digestion pattern as expected for an insert extending from the BamHI site in Ad5 to the right ITR.

Sequence analysis of the cloning border at the right ITR revealed that the most 3' G residue of the ITR was rnissing, the remainder of the ITR was found to be correct. The missing G residue is complemented by the other ITR during replication.

B. Generation of pBr/Ad.Sal-rITR (ECACC deposit P97082119)

pBr/Ad.Bam-rITR was digested with BamHI and SalI. The vector fragment including the adenovirus insert was isolated in LMP agarose (SeaPlaque GTG) and ligated to a 4.8 kb SalI-BamHI fragment obtained from wt Ad5 DNA and purified with the Geneclean II kit (Bio 101, Inc.). One clone was chosen and the integrity of the Ad5 sequences was determined by restriction enzyme analysis. Clone pBr/Ad.Sal-rITR contains adeno type 5 sequences from the SalI site at bp 16746 up to and including the rITR (missing the most 3' G residue).

C. pBr/Ad.Cla-Bam (ECACC deposit P97082117)

wt Adeno type 5 DNA was digested with ClaI and BamHI, and the 20.6-kb fragment was isolated from gel by electro-elution. pBr322 was digested with the same enzymes and purified from agarose gel by Geneclean. Both fragments were ligated and transformed into competent DH5a. The resulting clone pBr/Ad.Cla-Bam was analyzed by restriction enzyme digestion and shown to contain an insert with adenovirus sequences from bp 919 to 21566.

D. Generation of pBr/Ad.AflII-Bam (ECACC deposit P97082114)

Clone pBr/Ad.Cla-Bam was linearized with EcoRI (in pBr322) and partially digested with AflII. After heat inactivation of AflII for 20 minutes at 65° C. the fragment ends were filled in with Kienow enzyme. The DNA was then ligated to a blunt double stranded oligo linker containing a PacI site (5'-AATTGTCTTAATTAACCGCTTAA-3' (SEQ ID NO:3)). This linker was made by annealing the following two oligonucleotides: 5'-AATTGTCTTAATTAACCGC-3' (SEQ ID NO:4) and 5'-AATTGCGGTTAATTAAGAC-3' (SEQ ID NO:5), followed by blunting with Kienow enzyme. After precipitation of the ligated DNA to change buffer, the ligations were digested with an excess PacI enyme to remove concatemers of the oligo. The 22016 bp partial fragment containing Ad5 sequences from bp 3534 up to 21566 and the vector sequences, was isolated in LMP agarose (SeaPlaque GTG), re-ligated and transformed into competent DH5a. One clone that was found to contain the PacI site and that had retained the large adeno fragment was selected and sequenced at the 5' end to verify correct insertion of the PacI linker in the (lost) AflII site.

E. Generation of pBr/Ad.Bam-rITRpac#2 (ECACC deposit P97082120) and pBr/Ad.Bam-rITR#8 (ECACC deposit P97082121)

To allow insertion of a PacI site near the ITR of Ad5 in clone pBr/Ad.Bam-rITR about 190 nucleotides were removed between the ClaI site in the pBr322 backbone and the start of the ITR sequences. This was done as follows: pBr/Ad.Bam-rITR was digested with ClaI and treated with nuclease Bal131 for varying lengths of time 2 minutes, 5 minutes, 10 minutes and 15 minutes. The extent of nucleotide removal was followed by separate reactions on pBr322 DNA (also digested at the ClaI site), using identical buffers and conditions. Bal3I enzyme was inactivated by incubation at 75° C. for 10 minutes, the DNA was precipitated and re-suspended in a smaller volume TE buffer. To ensure blunt ends, DNA's were further treated with T4 DNA polymerase in the presence of excess dNTPs. After digestion of the (control) pBr322 DNA with SalI, satisfactory degradation (~150 bp) was observed in the samples treated or 10 minutes or 15 minutes. The 10 minutes or 15 minutes treated pBr/Ad.Bam-rITR samples were then ligated to the above-described blunted PacI linkers (See pBr/Ad.AflII-Bam). Ligations were purified by precipitation, digested with excess PacI and separated from the linkers on an LMP agarose gel. After re-ligation, DNA's were transformed into competent DH5a and colonies analyzed. Ten clones were selected that showed a deletion of approximately the desired length and these were further analyzed by T-track sequencing (T7 sequencing kit, Pharmacia Biotech). Two clones were found with the PacI linker inserted just downstream of the rITR. After digestion with PacI, clone #2 has 28 bp and clone #8 has 27 bp attached to the ITR.

F. Generation of pWE/Ad.AflII-rITR (ECACC deposit P97082116)

Cosmid vector pWE15 (Clontech) was used to clone larger Ad5 inserts. First, a linker containing a unique PacI site was inserted in the EcoRI sites of pWE15 creating pWE.pac. To this end, the double stranded PacI oligo as described for pBr/Ad.AflII-BamHI was used but now with its EcoR1 protruding ends. The following fragments were then isolated by electro-elution from agarose gel: pWE.pac digested with PacI, pBr/AflII-Bam digested with PacT and BamHI and pBr/Ad.Bam-rITR#2 digested with BamHI and PacI. These fragments were ligated together and packaged using 1 phage packaging extracts (Stratagene) according to the manufacturer's protocol. After infection into host bacteria, colonies were grown on plates and analyzed for presence of the complete insert. pWE/Ad.AflII-rITR contains all adenovirus type 5 sequences from bp 3534 (AflII site) up to and including the right ITR (missing the most 3' G residue).

G. Generation of pWE/Ad.AflII-EcoRI pWE.pac was digested with ClaI and 5' protruding ends were filled using Kienow enzyme. The DNA was then digested with PacT and isolated from agarose gel. pWE/AflII-rITR was digested with EcoRi and after treatment with Klenow enzyme digested with PacI. The large 24-kb fragment containing the adenoviral sequences was isolated from agarose gel and ligated to the ClaI-digested and blunted pWE.pac vector using the Ligation Express™ kit from Cliontech. After transformation of Ultra-competent XL10Gold cells from Stratagene, clones were identified that contained the expected insert. pWE/AflII-EcoRI contains Ad5 sequences from bp 3534–27336.

H. Generatron of pWE/Ad.AflII-rITRDE2A:

Deletion of the E2A coding sequences from pWE/Ad.AflII-rITR (ECACC deposit P97082116) has been accomplished as follows. The adenoviral sequences flanking the E2A coding region at the left and the right site were amplified from the plasmid pBr/Ad.Sal.rITR (ECACC deposit P97082119) in a PCR reaction with the Expand PCR system (Boehringer) according to the manufacturers protocol. The following primers were used: Right flanking sequences (corresponding Ad5 nucleotides 24033 to 25180):
DE2A.SnaBI: 5'-GGC GTA CGT AGC CCT GTC GAA AG-3'(SEQ ID NO:6) DE2A.DBP-start: 5'-CCA *ATG CAT* TCG AAG TAC TTC CTT CTC CTA TAG GC-3'(SEQ ID NO:7)

The amplified DNA fragment was digested with SnaBI and NsiI (NsiI site is generated in the primer DE2A.DBP-start, underlined). In addition, a unique BstBI site is generated in this primer (italics).

Left flanking sequences (corresponding Ad5 nucleotides 21557 to 22442):
  DE2A.DBP-stop: 5'-CCA *ATG CAT* ACG GCG CAG ACG G-3'(SEQ ID NO:8)
  DE2A.BamHI: 5'-GAG GTG GAT CCC ATG GAC GAG-3'(SEQ ID NO:9)

The amplified DNA was digested with BamHI and NsiI (NsiI site is generated in the primer DE2A.DBP-stop, underlined). Subsequently, the digested DNA fragments were ligated into SnaBI/BamHI digested pBr/Ad.Sal-rITR. Sequencing confirmed the exact replacement of the DBP coding region with a unique NsiI site and BstBI site in plasmid pBr/Ad.Sal-rITRDE2A. The unique NsiI site and BstBI site can be used to introduce an expression cassette for a gene to be transduced by the recombinant vector.

The deletion of the E2A coding sequences was performed such that the splice acceptor sites of the 100K encoding L4-gene at position 24048 in the top strand was left intact. In addition, the polyadenylation signals of the original E2A-RNA and L3-RNAs at the left hand site of the E2A coding sequences were left intact. This ensures proper expression of the IL3-genes and the gene encoding the 100K L4-protein during the adenovirus life cycle.

Next, the plasmid pWE/Ad.AflII-rITRDE2A was generated. The plasmid pBr/Ad.Sa1-rITRDE2A was digested with BamHI and SpeI. The 3.9-Kb fragment in which the E2A coding region was replaced by the unique NsiI site and BstBI site was isolated. The pWE/Ad.AflII-rITR was digested with BamHI and SpeI. The 35 Kb DNA fragment, from which the BamHII/SpeI fragment containing the E2A coding sequence was removed, was isolated. The fragments were ligated and packaged using 1 phage-packaging extracts according to the manufacturer protocol (Stratagene), yielding the plasmid pWE/Ad.AflII-rITRDE2A. Note that there is no sequence overlap between the adenoviral sequences present in pWE/Ad.AflII-rITRDE2A and the E2A sequences present in the expression vectors pcDNA3tsE2A and pcDNAwtE2A or the cell lines derived from this vector.

I. Generation of the Adapter Plasmids

Adapter plasmid pMLP.TK (European patent application no. EP 95202213) was modified as follows: SV40 polyA sequences were amplified with primer SV40-1 (introduces a BamHI site) and SV40-2 (introduces a BglII site). In addition, Ad5 sequences present in this construct (from nt. 2496 to nt. 2779; Ad5 sequences nt. 3511 to 3794) were amplified with primers Ad5-1 (introduces a BglII site) and Ad5-2.

SV40 1:
5'-GGGGGATCCGAACTTGTTTTATTGCAGC-3' (SEQ ID NO:10).

SV402: 5'-GGGAGATCTAGACATGATAAGATAC-3' (SEQ ID NO:11).

Ad5-1: 5'-GGGAGATCTGTACTGAAATGTGTGGGC-3'(SEQ ID NO:12).

Ad5-2: 5'-GGAGGCTGCAGTCTCCAACGGCGT-3' (SEQ ID NO:13).

Both PCR fragments were digested with BglII and ligated. The ligation product was amplified with primers SV40-1 and Ad5-2 and digested with BamHI and AflII. The digested fragment was then ligated into pMLP.TK predigested with the same enzymes. The resulting construct, named pMLPI.TK, contains a deletion in adenovirus E1 sequences from nt. 459 to nt. 3510.

This plasmid was used as the starting material to make a new vector in which nucleic acid molecules comprising specific promoter and gene sequences can be easily exchanged. First, a PCR fragment was generated from pZipDMo+PyF101(N⁻) template DNA (described in PCT/NL96/00195) with the following primers: LTR-1: 5'-CTG TAC GTA CCA GTG CAC TGG CCT AGG CAT GGA AAA ATA CAT AAC TG-3'(SEQ ID NO:14) and LTR-2: 5'-GCG GAT CCT TCG AAC CAT GGT AAG CTT GGT ACC GCT AGC GTT AAC CGG GCG ACT CAG TCA ATC G-3'(SEQ ID NO:15). Pwo DNA polymerase (Boehringer Mannheim) was used according to manufacturers protocol with the following temperature cycles: once 5 minutes at 95° C.; 3 minutes at 55° C.; and 1 minute at 72° C., and 30 cycles of 1 minute at 95° C., 1 minute at 60° C., 1 minute at 72° C., followed by once for 10 minutes at 72° C. The PCR product was then digested with BamHI and ligated into PMLP10 (Levrero et al., 1991; Gene 101, 195–202) digested with PvuII and BamHI, thereby generating vector pLTR10. This vector contains adenoviral sequences from bp 1 up to bp 454 followed by a promoter consisting of a part of the Mo-MuLV LTR having its wild-type enhancer sequences replaced by the enhancer from a mutant polyoma virus (PyF101). The promoter fragment was designated L420. Sequencing confirmed correct amplification of the LTR fragment; however, most 5' bases in the PCR fragment were missing so that the PvuII site was not restored. Next, the coding region of the murine HSA gene was inserted. pLTR10 was digested with BstBI followed by Klenow treatment and digestion with NcoI. The HSA gene was obtained by PCR amplification on pUC18-HSA (Kay et al., 1990; J. Immunol. 145, 1952–1959) using the following primers: HSA1, 5'-GCG CCA CCA TGG GCA GAG CGA TGG TGG C-3'(SEQ ID NO:16) and HSA2, 5'-GTT AGA TCT AAG CTT GTC GAC ATC GAT CTA CTA ACA GTA GAG ATG TAG AA-3'(SEQ ID NO:17). The 269 bp-amplified fragment was sub-cloned in a shuttle vector using the NcoI and BglII sites. Sequencing confirmed incorporation of the correct coding sequence of the HSA gene, but with an extra TAG insertion directly following the TAG stop codon. The coding region of the HSA gene, including the TAG duplication, was then excised as a NcoI (sticky)-SalI (blunt) fragment and cloned into the 3.5 kb NcoI (sticky)/BstBI (blunt) fragment from pLTR10, resulting in pLTR-HSA10.

Finally, pLTR-HSA10 was digested with EcoRI and BamHI after which the fragment containing the left ITR, packaging signal, L420 promoter and HSA gene was inserted into vector pMLPI.TK digested with the same enzymes and thereby replacing the promoter and gene sequences. This resulted in the new adapter plasmid pAd5/L420-HSA that contains convenient recognition sites for various restriction enzymes around the promoter and gene sequences. SnaBI and AvrII can be combined with HpaI, NheI, KpnI, and HindIII to exchange promoter sequences, while the latter sites can be combined with the ClaI or BamHI sites 3' from HSA coding region to replace genes in this construct.

Another adapter plasmid that was designed to allow easy exchange of nucleic acid molecules was made by replacing the promoter, gene and polyA sequences in pAd5/L420-HSA with the CMV promoter, a multiple cloning site, an intron and a polyA signal. For this purpose, pAd/LA420-HSA was digested with AvrII and BglII followed by treatment with Klenow to obtain blunt ends. The 5.1 kb fragment with pBr322 vector and adenoviral sequencs was isolated and ligated to a blunt 1570 bp fragment from pcDNA1/amp (Invitrogen) obtained by digestion with HhaI and AvrII followed by treatment with T4 DNA polymerase. This adapter plasmid was named pAd5/Clip.

The adapter plasmid pCMV.LacZ was generated as follows: The plasmid pCMV.TK (EP 95-202 213) was digested with HindIII, blunted with Klenow and dNTPs and subsequently digested with SalI. The DNA fragment containing the CMV promoter was isolated. The plasmid pMLP.nlsLacZ (EP 95-202 213) was digested with KpnI, blunted with T4 DNA polymerase and subsequently digested with SalI. The DNA fragment containing the LacZ gene and adjacent adenoviral sequences was isolated. Next, the two DNA fragments were ligated with T4 DNA ligase in the presence of ATP, giving rise to pCMV.nlsLacZ.

The adapter plasmid pAd5/CLIP.LacZ was generated as follows: The *E. coli* LacZ gene was amplified from the plasmid pMLP.nlsLacZ (EP 95-202 213) by PCR with the primers 5'GGGGTGGCCAGGGTACCTCTAG-GCITTTGCAA (SEQ ID NO:18) and 5'GGGGGGGATC-CATAAACAAGTTCAGAATCC (SEQ ID NO:19). The PCR reaction was performed Ex Taq (Takara) according to the suppliers protocol at the following amplification program: 5 minutes 94° C., 1 cycle; 45 seconds 94° C. and 30 seconds 60° C. and 2 minutes 72° C., 5 cycles; 45 seconds 94° C. and 30 seconds 65° C and 2 minutes 72° C. 25 cycles; 10 minutes 72° C., 1clcle; 45seconds 94° C. and 30 seconds 60° C. and 2 minutes 72° C., 5 cycles, I cycle. The PCR product was subsequently digested with Kpn1 and BamHI and the digested DNA fragment was ligated into KpnI/BamHI digested pcDNA3 (Invitrogen), giving rise to pcDNA3.nlsLacZ. Next, the plasmid pAd/CLIP was digested with SpeI. The large fragment containing part of the 5' part CMV promoter and the adenoviral sequences was isolated. The plasmid pcDNA3.nlsLacZ was digested with SpeI and the fragment containing the 3' part of the CMV promoter and the LacZ gene was isolated. Subsequently, the fragments were ligated, giving rise to pAd/CUP.LacZ. The reconstitution of the CMV promoter was confirmed by restriction digestion.

The adapter plasmid pAd5/CLIP.Luc was generated as follows: The plasmid pCMV.Luc (EP 95-202 213) was digested with HindIII and BamHI. The DNA fragment containing the luciferase gene was isolated. The adapter plasmid pAd/CLIP was digested with HindIII and BamHI, and the large fragment was isolated. Next, the isolated DNA fragments were ligated, giving rise to pAd5/CLIP.Luc.

EXAMPLE III

Generation of Recombinant Adenoviruses

A. E1-deleted Recombinant Adenoviruses with wt E3 Sequences

To generate E1 deleted recombinant adenoviruses with the plasmid-based system, the following constructs are prepared:

a) An adapter construct containing the expression cassette with the gene of interest linearized with a restriction enzyme that cuts at the 3' side of the overlapping adenoviral genome fragment, preferably not containing any pBr322 vector sequences, and b) A complementing adenoviral genome construct pWE/Ad.AflII-rITR digested with PacI.

These two DNA molecules are further purified by phenol/chloroform extraction and ethanol precipitation. Co-transfection of these plasmids into an adenovirus packaging cell line, preferably a cell line according to the invention, generates recombinant replication deficient adenoviruses by a one-step homologous recombination between the adapter and the complementing construct.

A general protocol as outlined hereinafter and meant as a non-limiting exanple of the present invention has been performed to produce several recombinant adenoviruses using various adapter plasmids and the Ad.AflII-rITR fragment. Adenovirus packaging cells (PER.C6) were seeded in ~25 cm² flasks and the next day when they were at ~80% confluency, transfected with a mixture of DNA and lipofectamine agent (Life Techn.) as described by the manufacturer. Routinely, 40 $\mu$l lipofectamine, 4 $\mu$g adapter plasmid and 4 $\mu$g of the complementing adenovirus genome fragment AflII-rITR (or 2 $\mu$g of all three plasmids for the double homologous recombination) are used. Under these conditions, transient transfection efficiencies of ~50% (48 hrs post transfection) are obtained as determined with control transfections using a pAd/CMV-LacZ adapter. Two days later, cells are passaged to ~80 cm² flasks and further cultured. Approximately five (for the single homologous recombination) to eleven days (for the double homologous recombination) later a cytopathic effect (CPE) is seen, indicating that functional adenovirus has formed. Cells and medium are harvested upon full CPE and recombinant virus is released by freeze-thawing. An extra amplification step in a 80 cm² flask is routinely performed to increase the yield since at the initial stage the titers are found to be variable despite the occurrenee of full CPE. After amplification, viruses are harvested and plaque purified on PER.C6 cells. Individual plaques are tested for viruses with active trasgenes.

Several different recombinant adenoviruses, compri s ing the luciferase gene (IG.Ad.CLIP.Luc), the bacterial LacZ gene (IG.Ad.CLIP.LacZ and IG.Ad.CMV.LacZ) or an empty CLIP cassette (IG.Ad.CLIP) have been produced using this protocol. In all cases, functional adenovirus was formed and all isolated plaques contained viruses with the expected expression cassettes.

B. Generation of Recombinant Adenoviruses Deleted for E1 and E2A

Besides replacements in the E1 region, it is possible to delete or replace the E2A region in the adenovirus. This creates the opportunity to use a larger insert or to insert more than one gene without exceeding the maximum packagable size (approximately 105% of wt genome length).

Recombinant viruses that are both E1 and E2A deleted are generated by a homologous recombination procedure as described above for E1-replacement vectors using a plasmnid-based system consisting of:

a) An adapter ptid for E1 replacement according to the invention, with or without insertion of a first gene of interest.

b) The pWE/Ad.AflII-rITRDE2A fragment, with or without insertion of a second gene of interest.

Generation and propagation of such viruses, e.g., IG.Ad.CMV.LacZDE2A, IG.Ad.CLIP.LacZDE2A, IG.Ad.CLIPDE2A or IG.Ad.CLIP.LucDE2A, requires a complementing cell line for complementation of both E1 and E2A proteins in trans, as previously described herein.

In addition to replacements in the E1 and E2A region, it is also possible to delete or replace (part of) the E3 region in the E1-deleted adenoviral vector, because B3 functions are not necessary for the replication, packaging and infection of the (recombinant) virus. This creates the opportunity to use larger inserts or to insert more than one gene without exceeding the maximum packagabde size (a pproximately 105% of wt genome length). This ca n be done, e.g., by deleting part of the E3 region in the pBr/Ad.Bam-rITR clone by digestion with XbaI and re-ligation. This removes Ad5 wt sequences 28592–30470 including all known E3 coding regions. Another example is the precise replacement of the coding region of gp19K in the E3 region with a polylinker allowing insertion of new sequences. This, 1) leaves all other coding regions intact and 2) obviates the need for a heterologous promoter since the transgene is driven by the E3 promoter and pA sequences, leaving more space for coding sequences.

To this end, the 2.7-kb EcoRI fragment from wt Ad5 containing the 5' part of the E3 region was cloned into the EcoRI site of pBluescript (KS⁻) (Stratagene). Next, the HinduIII site in the polylinker was removed by digestion with EcoRV and HincII and subsequent re-ligation. The resulting clone pBS.Eco-Eco/ad5DHIII was used to delete the gp19K-coding region. Primers 1 (5'-GGG TAT TAG GCC AAA GGC GCA-3'(SEQ ID NO:20)) and 2 (5'-GAT CCC ATG GAA GCT TGG GTG GCG ACC CCA GCG-3' (SEQ ID NO:21)) were used to amplify a sequence from pBS.Eco-Eco/ad5DHIII corresponding to sequences 28511 to 28734 in wt Ad5 DNA. Primers 3 (5'-GAT CCC ATG GGG ATC CTT TAC TAA GTT ACA AAG CTA-3'(SEQ ID NO:22)) and 4 (5'-GTC GCT GTA GTT GGA CTG G-3' (SEQ ID NO:23)) were used on the same DNA to amplify Ad5 sequences from 29217 to 29476. The two resulting PCR fragments were ligated together by virtue of the new introduced NcoI site and subsequently digested with XbaI and MunI. This fragment was then ligated into the pBS.Eco-Eco/ad5DHIII vector that was digested with XbaI (partially) and MunI generating pBS.Eco-Eco/ad5DHIII.Dgp19K. To allow insertion of foreign genes into the HindIII and BamHI site, an XbaI deletion was made in pBS.Eco-Eco/ad5DHIII.Dgp19K to remove the BamHI site in the Bluescript polylinker. The resulting plasmid pBS.Eco.Eco/ad5DHIII.Dgp19KDXbaI, contains unique HindIII and BamHI sites corresponding to sequences 28733 (HindIII) and 29218 (BamHI) in Ad5. After introduction of a foreign gene into these sites, either the deleted XbaI fragment is re-introduced, or the insert is re-cloned into pBS.Eco-Eco/ad5DHIII.Dgp19K using HindIII and, for example, MunI. Using this procedure, we have generated plasmids expressing HSV-TK, hIL-1a, rat IL-3, luciferase or LacZ. The unique SrfI and NotI sites. in the pBS.Eco-Eco/ad5DHIII.Dgp19Kplasmid (with or without inserted gene of interest) are used to transfer the region comprising the gene of interest into the corresponding region of pBr/Ad.Bam-rITR, yielding construct pBr/Ad.Bam-rITRDgp19K (with or without inserted gene of interest). This construct is used as described supra to produce recombinant adenoviruses. In the viral context, expression of inserted genes is driven by the adenovirus E3 promoter.

Recombinant viruses that are both E1 and E3 deleted are generated by a double homologous recombination procedure for E1-replacement vectors using a plasmid-based system consisting of:

a) an adapter plasmid for E1 replacement according to the invention, with or without insertion of a first gene of interest, b) the pWE/Ad.AflII-EcoRI fragment, and c) the pBr/Ad.Bam-rITRDgp19K plasmid with or without insertion of a second gene of interest.

In addition to manipulations in the E3 region, changes of (parts of) the E4 region can be accomplished easily in pBr/Ad.Bam-rITR. Moreover, combinations of manipulations in the E3 and/or E2A and/or E4 region can be made. Generation and propagation of such vectors, however, demands packaging cell lines that complement for E1 and/or E2A and/or E4 in trans.

EXAMPLE IV

E2A Revertant-free Manufacturing of E1/E2A Deleted Vectors on PER.C6/E2A Cells.

The cell lines and E1/E2A deleted vectors described hereinbefore are developed such that overlap between sequences in the recombinant adenoviral genome and E2A sequences in the complementing cell lines is avoided. This eliminates reversion of the E2A-deleted phenotype in the E1/E2A deleted recombinant adenoviral vectors due to homologous recombination. The occurrence of reversion of the E2A deleted phenotype was studied in a PCR assay.

PERC6tsE2A clone 3–9 cells were cultured in DMEM supplemented with 10% FBS and 10 mM $MgCl_2$ in a 10% $CO_2$ atmosphere at 39° C. in a 25 $cm^2$ tissue culture flask. At 50% confluency, cells were infected with the recombinant adenoviral vector IG.Ad.CMV.LacZDE2A and the cells were put at 32° C. Four days post infection CPE appeared and the cells were harvested by flicking the flask. Cells were pelleted by centrifugation and the cell pellet was re-suspended in 1 ml/10 mM phosphate buffer (18 ml 0.2M $Na_2HPO_4$ (Baker) and 7 ml 0.2M $NaH_2PO_4$ (Merck) in 500 ml $H_2O$ pH=7.2). Next, 200 µl 5% sodium deoxycholate (Sigma) was added. The mixture was incubated for 30 minutes at 37° C. and 50 µl 1M $MgCl_2$ and 10 µl DNase (1MU/ml; ICN) was added. The mixture was incubated for another half hour at 37° C. and than cleared by centrifugation. The supernatant was put into a new tube and 100 µl 10% SDS (Baker) and 5 µl Proteinase K (20 mg/ml; Boehringer) were added. The mixture was incubated for 30 minutes at 37° C. and subsequently for 15 minutes at 65° C.. Next, 1 ml phenol (Sigma) was added and the mixture was tumbled for 1 hour and centrifuged. One ml of supernatant was put into a fresh tube and 1 ml chloroform (Baker) was added. The mixture was tumbled for another 30 minutes and centrifuged. The supernatant was put into a fresh tube and mixed with 1 ml 2-Propanol (Baker) and the DNA was pelleted by centrifugation. The DNA was washed in 70% Ethanol (Baker) and re-suspended in 200 µl TE and 1 µl RNase (10 mg/ml; Boehringer). The DNA concentration was determined at a spectrophotometer.

The recombinant adenoviral vector DNA was screened for reversion of the E2A deleted phenotype by PCR. Two PCR reactions were performed (FIG. 7). The first was a nested PCR reaction for the detection of E2A sequences in the DNA sample. Two primer sets were designed. Set A contains the primers 551: 5'CCGGCAAGTCTTGCGGCATG (SEQ ID NO:24) and 556: 5'TAGCAGGTCGGGCGCCGATAT (SEQ ID NO:25) and the nested primers 553: 5'GGCTCAG-GTGGCTTTTAAGCAG (SEQ ID NO:26) and 554: 5'GAGTTGCGATACACAGGGTTGC (SEQ ID NO:27). The PCR reaction was performed using the eLONGase enzyme mix (Gibco) according to the manufacturer's protocol. DNA from $1\times10^9$ viral particles (+), which is equivalent to ~40 ng, or water (-) was added as template. The PCR reactions were either not spiked, or spiked with 1, 10 and 40 molecules pBR/Ad.Sal-rITR, respectively, as indicated in FIG. 7. The following amplification program for the PCR reaction with primers 551 and 556 was used: 30 seconds at 94° C., 1 cycle; 30 seconds 94° C.. and 30 seconds at 66° C.. and 90 seconds at 68° C.., 35 cycles; 10 minutes 68° C.., 1 cycle. One µl of this reaction was put into a nested PCR with primers 553 and 554 at the following amplification program: 30 seconds at 94° C.., 1 cycle; 30 seconds at 94° C. and 30 seconds at 66° C.. and 90 seconds at 68° C.., 35 cycles; 10 minutes 68° C.., 1 cycle. This reaction yields a DNA fragment of 260 bp.

In the second PCR reaction, a set of primers (Set B) was used that flank the E2A gene in the adenoviral genome on the left and the right hand site. This PCR reaction amplifies a DNA fragment spanning the site from which the E2A gene was deleted (FIG. 6). Primer set B comprises primer 731 5'AGTGCGCAGATTAGGAGCGC (SEQ ID NO:28) and primer 734 5'TCTGCCTATAGGAGAAGGAA (SEQ ID NO:29). The PCR reaction was performed using the eLONGase enzyme mix (Gibco) according to the manufacturer protocol. DNA from $1\times10^9$ viral particles (+), which is equivalent to ~4 ng, or water (-) was added as template. The PCR reactions were either not spiked, or spiked with 1, 10 and 40 molecules pBR/Ad.Sal-rITR, respectively, as indicated in FIG. 7. The following amplification program was used: 30 seconds at 94° C.., 1 cycle; 30 seconds 94° C.. and 30 seconds at 50° C. and 90 seconds at 68° C., 35 cycles; 10 minutes 68° C. 1 cycle. This PCR reaction yields a DNA fragment of 169 bp.

As shown in FIG. 7, left panel (set A), E2A sequences were amplified from the DNA samples (+) and control samples (−) spiked with both 1, 10 and 40 molecules, as evidenced by the amplification of a 260 bp DNA fragment. In contrast, no E2A sequences were amplified from the non-spiked samples. This shows that reversion of the E2A-deleted does not occur. The PCR reactions with primers 731/734 yielded the expected DNA fragment of 169 bp in the samples containing the recombinant adenoviral vector DNA (+). From the negative control samples containing the water instead of DNA (−), no DNA fragment of 169 bp was amplified. These data show that elimination of overlap between adenoviral sequences in the vector and cell line prevents reversion of the E2A-deleted phenotype.

EXAMPLE V

Transduction Capacity of and Residual Expression of Adenoviral Genes from E1-deleted and E1/E2A-deleted Recombinant Adenoviral Vectors The transduction capacity of E1/E2A deleted vectors was compared to E1 deleted vectors. HeLa cells were seeded at $5\times10^5$ cells/well in 6 well plates (Greiner) in DMEM supplemented with 10% FBS in a 10% $CO_2$ atmosphere at 37° C.. The next day, cells were infected with a m.o.i. of either 0, 10, 100 or 1000 viral particles IG.Ad/CMV.LacZ or IG.Ad/CMV.LacZDE2A per cell. Forty-eight hours post infection, cells were washed with PBS (NPBI) and fixed for 8 minutes in 0.25% glutaraldehyde (Sigma) in PBS (NPBI). Subsequently, the cells were washed twice with PBS and stained for 8 hours with X-gal solution (1 mg/ml X-gal in DMSO (Gibco), 2 mM $MgCl_2$ (Merck), 5 mM $K_4[Fe(CN)_6].3H_2O$ (Merck), 5 mM $K_3[Fe(CN)_6]$ (Merck) in PBS. The reaction was stopped by removal of the X-gal solution and washing of the cells with PBS. FIG. 8 shows that IG.Ad/CMV.LacZDE2A transduced HeLa cells at least as good as did IG.Ad/CMV.LacZ at all m.o.i.'s. Comparable results were obtained after infection of IG.Ad.CLIP.LacZ and IG.Ad.CLIP.LacZDE2A and after infection of A549 cells with the respective recombinant adenoviral vectors. These data show that the viral particle to transduction unit ratio (vp/tu) of E1/E2A deleted vectors (e.g., IG.Ad/CMV.LacZDE2A) is at least as good as the vp/tu of E1 deleted vectors (e.g., IG.Ad/CMV.LacZ).

Next, the vp/tu ratio of E1- and E1/E2A-deleted vectors was determined in a more sensitive assay, i.e., a luciferase assay. HeLa and A549 cells were seeded at $5\times10^5$ cells/well in 6 well plates (Greiner) in DMEM supplemented with 10% FBS in a 10% $CO_2$ atmosphere at 37° C. The next day, cells were infected with a m.o.i. of either 0, 10, 100, 1,000 or 10,000 vp/cell IG.Ad/CLIP.Luc or IG.Ad/CLIP.LucDE2A per cell. Two days post infection, cells were lysed and the luciferase activity was determined with the Luciferase Assay System according to the protocol of the supplier (Promega). FIG. 9 shows that both the IG.Ad/CLIP.LucDE2A infected HeLa and A549 cells produce more luciferase enzyme than the IG.Ad/CLIP.Luc infected HeLa and A549 and HeLa cells, at all m.o.i.'s tested. These data confirm that E1/E2A deleted recombinant adenoviral vectors produced on PER.C6ts125E2A cells have a vp/tu ratio that is at least as good as the vp/tu ratio of E1 deleted vectors. The above is in contrast to what has recently been reported by others (O'Neal et al., 1998; Lusky et al., 1998), who found that the vp/tu ratio of E1/E2A deleted recombinant adenoviral vectors is impaired significantly. However, these vectors were produced on two independent 293 based E2A complementing cell lines harboring inducible E2A genes. This suggests that the use of temperature sensitive E2A genes, such as ts125E2A, yields superior E2A complementing cell lines as compared to the commonly used inducible E2A genes.

In order to test whether E1/E2A deleted vectors residually express adenoviral proteins, the following experiment has been performed. A549 cells were seeded on 6 well plates (Greiner) at a density of $5\times10^5$ cells/well in DMEM supplemented with 10% FBS in a 10% $CO_2$ atmosphere at 37° C. The next day, cells were infected with a m.o.i. of either 0, 100, 1,000 or 10,000 vp/cell IG.Ad/CLIP or IG.Ad.CLIPDE2A. After 12 hours, the infection medium was replaced by fresh DMEM supplemented with 10% FBS. Seventy-two hours post infection, the cells were washed with PBS (NPBI) and lysed and scraped in RIPA (1% NP-40, 0.5% sodium deoxycholate and 0.1% SDS in PBS, supplemented with 1 mM phenylmethylsulfonylfluoride and 0.1 mg/ml trypsin inhibitor). After 15 minutes incubation on ice, the lysates were cleared by centrifugation. Protein concentrations were determined by the BioRad protein assay, according to standard procedures of the supplier (BioRad). Equal amounts of whole-cell extract were fractionated by SDS-PAGE on 10% gels in triplicate. Proteins were transferred onto Immobilon-P membranes (Millipore) and incubated with the aDBP monoclonal antibody B6, the polyclonal a-Penton base antibody Ad2-Pb571 (kind gift of Dr. P. Boulanger, Montpellier, France) and the polyclonal a-knob domain antibody of fiber E641/3 (kind gift of R. Gerard, Leuven, Belgium). The secondary antibodies were a horseradis-hperoxidase-conjugated goat anti mouse and a horseradish-peroxidase-conjugated goat anti rabbit (BioRad). The Western blotting procedure and incubations were performed according to the protocol provided by Millipore. The complexes were visualized with the ECL detection system according to the manufacturer's protocol (Amersham). FIG. 10 shows that cells infected with IG.Ad-.CLIP express both E2A encoded DBP, Penton base and Fiber proteins. The proteins co-migrated with the respective proteins in the positive control (lane P, extract from PER.C6 cells infected with IG.Ad.CLIP harvested at starting CPE). The residual expression of these proteins in A549 cells was m.o.i. dependent. In contrast, no DBP, penton-base or fiber was detected in the non-infected A549 cells or cells infected with IG.Ad.CLIPDE2A. These data show that deletion of the E2A gene did not only eliminate residual DBP expression, but also the residual expression of the late adenoviral proteins, penton-base and fiber.

In conclusion, the foregoing shows that E1/E2A deleted vectors produced on PER.C6/tsE2A complementing cell lines have a favorablephenotype. First, these vectors have an ideal vp/tu ratio, which is at least as good as that of E1 deleted vectors. Second, the E1/E2A deleted vectors do not residually express detectable anounts of E2A encoded DBP or late gene encoded penton-base or fiber. This favorable phenotype improves the prospects for the use of recombinant adenoviral vectors in gene therapy.

What is claimed is:

1. A cell capable of at least in part complementing adenovirus E2A function of an adenovirus defective in E2A function, said cell comprising a nucleic acid encoding adenovirus E2A or a functional part thereof, wherein said nucleic acid encoding adenovirus E2A encodes a temperature sensitive E2A mutant.

2. The cell of claim 1, wherein said temperature sensitive E2A mutant is an E2A mutant encoded by adenovirus ts125.

3. A cell capable of at least in part complementing adenovirus E2A function of an adenovirus defective in E2A function, said cell comprising PER.C6 (ECACC deposit number 96022940), said PER.C6 further comprising a nucleic acid encoding adenovirus E2A or a functional part thereof.

4. A method for producing an adenoviral particle containing an adenovirus vector with a functional deletion of E2A, said method comprising:

providing a cell with a replication deficient adenovirus vector defective in E1 and E2A function, said cell further:

being capable of at least in part complementing adenovirus E2A function of an adenovirus defective in E2A function, comprising a nucleic acid encoding adenovirus E2A or a functional part thereof, integrated into said cell's genome, and further comprising a nucleic acid sequence encoding adenovirus E1-region proteins or a functional part thereof, wherein said nucleic acid sequence encoding adenovirus E1-region proteins or a functional part thereof has no sequence overlap with said replication defective adenovirus vector which leads to replication competent adenovirus and/or to the formation of an adenovirus vector comprising an E1 function, culturing said cell, and harvesting said adenoviral particle.

5. The method according to claim 4, wherein said adenovirus vector further comprises at least one nucleic acid of interest.

6. The method according to claim 4, wherein said nucleic acid sequence encoding adenovirus E1-region proteins or a functional part thereof, is integrated into said cell's genome.

7. An adenovirus vector deficient in E2A function, said vector obtained by omitting nucleotides 22443 to 24032 in adenovirus 5.

8. The adenovirus vector of claim 7, further comprising at least one nucleic acid of interest.

9. A replication deficient adenovirus vector obtained by omitting nucleotides 459 to 3510 in adenovirus 5.

10. An adenovirus vector defective in E2A function, obtained by excluding a region which in adenovirus 5 corresponds to nucleotides 22443–24032.

11. The adenovirus vector of claim 10 further comprising at least nucleic acid which in adenovirus 5 corresponds to nucleotides 3534–22417 and/or nucleotides 24038 until the right ITR.

12. The adenovirus vector of claim 10 further comprising at least nucleic acid which in adenovirus 5 corresponds to nucleotides 3534–22442 and/or nucleotides 24033 until the right ITR.

13. The adenovirus vector of claim 10 further comprising at least nucleic acid which in adenovirus 5 corresponds to nucleotides 3534–22442 and/or nucleotides 24033 until the right ITR.

14. An adenovirus vector defective in E2A function, obtained by excluding a region which in adenovirus 5 corresponds to nucleotides 22418–24037.

15. An adenovirus vector defective in E2A function, obtained by excluding a region which in adenovirus 5 corresponds to nucleotides 22348–24060.

16. A cell capable of at least in part complementing adenovirus E2A function of an adenovirus defective in E2A function, said cell comprising a nucleic acid encoding adenovirus E2A or a functional part thereof, wherein said nucleic acid is integrated into said cell's genome and further comprising a nucleic acid sequence encoding adenovirus E1-region proteins or a functional part thereof, wherein said nucleic acid encoding adenovirus E1-region proteins or a functional part thereof has no sequence overlap with a replication defective adenovirus vector defective in E1 which leads to replication competent adenovirus and/or to the formation of an adenovirus vector comprising an E1 function.

* * * * *

UNITED STATES PATENT AND TRADEMARK OFFICE
CERTIFICATE OF CORRECTION

PATENT NO.    : 6,395,519 B1
DATED         : May 28, 2002
INVENTOR(S)   : Frits J. Fallaux et al.

It is certified that error appears in the above-identified patent and that said Letters Patent is hereby corrected as shown below:

Title page,
Item [56], References Cited, FOREIGN PATENT DOCUMENTS,
"97/05255" change "Wo" to -- WO --
Item [57], ABSTRACT,
Line 9, change "finctional" to -- functional --

Column 1,
Line 9, delete "pending"

Column 2,
Line 43, change "(Kiessig" to -- (Klessig --

Column 3,
Line 18, change "transfecfion" to -- transfection --

Column 5,
Line 13, change "fuinctional" to -- functional --
Line 14, insert a period after "thereof"
Line 26, change "finctionally" to -- functionally --
Line 61, change "ini" to -- in --

Column 6,
Line 4, change "adenoviws" to -- adenovirus --
Line 6, change "vectorpreferably" to -- vector preferably --

Column 7,
Line 3, change "CG<u>G TA CC</u>G CCA CCA" to -- CG<u>G GAT CC</u>G *CCA CCA* --
Line 43, change "PBR.C6" to -- PER.C6 --
Line 45, change "$2 \times 10^4$" to -- $2 \times 10^6$ --

Column 8,
Line 32, change "deternined" to -- determined --

Column 9,
Line 23, change "sixteen" to -- Sixteen --
Line 49, change "wholecell" to -- whole-cell --

Column 11,
Line 56, change "serumrfree" to -- serum free --
Line 59, change "PER.C6/2A" to -- PER.C6/E2A --

UNITED STATES PATENT AND TRADEMARK OFFICE
CERTIFICATE OF CORRECTION

PATENT NO. : 6,395,519 B1
DATED : May 28, 2002
INVENTOR(S) : Frits J. Fallaux et al.

It is certified that error appears in the above-identified patent and that said Letters Patent is hereby corrected as shown below:

Column 12,
Line 12, change "werewashed" to -- were washed --
Line 47, change "Kienow" to -- Klenow --
Line 61, change "rnissing" to -- missing --

Column 13,
Lines 23 and 29, change "Kienow" to -- Klenow --
Line 48, change "Bal131" to -- Bal31 --

Column 14,
Line 26, change "Kienow" to -- Klenow --
Line 27, change "PacT" to -- PacI --
Line 28, change "EcoRi" to -- EcoRI --
Line 33, change "Cliontech" to -- Clontech --
Line 34, change "XL10Gold" to -- XL10-Gold --
Line 37, change "Generatron" to -- Generation --
Lines 48-49, change "CAT TCG AAG" to -- *CAT TCG AAG* --

Column 15,
Line 7, change "left hand" to -- left-hand --
Line 9, change "IL3" to -- L3 --
Line 35, change "S V 4 0 1 :" to -- SV40-1: --
Line 38, change "SV402:" to -- SV40-2: --
Lines 62-63, change "manufacturers" to -- manufacturer's --

Column 16,
Line 49, change "sequencs" to -- sequences --

Column 17,
Line 2, change "GCITTTGCAA" to -- GCTTTTGCAA --
Line 9, change "lclcle; 45seconds" to -- ; 45 seconds --
Line 20, change "pAd/CUP.LacZ." to -- pAd/CLIP.LacZ. --
Line 54, change "exanple" to -- example --

UNITED STATES PATENT AND TRADEMARK OFFICE
CERTIFICATE OF CORRECTION

PATENT NO.    : 6,395,519 B1
DATED         : May 28, 2002
INVENTOR(S)   : Frits J. Fallaux et al.

It is certified that error appears in the above-identified patent and that said Letters Patent is hereby corrected as shown below:

Column 18,
Line 10, change "occurrenee" to -- occurrence --
Line 14, change "compri s ing" to -- comprising --
Line 31, change "plasmnid-based" to -- plasmid-based --
Line 44, change "B3" to -- E3 --
Line 48, change "a pproximately" to -- approximately --
Line 49, change "ca n" to -- can --
Line 63, change "HinduIII" to -- HindIII --

Column 19,
Line 17, change "pBS.Eco.Eco/" to -- pBS.Eco-Eco/ --
Line 26, delete the period after "sites"
Line 66, change "PERC6tsE2A" to -- PER.C6tsE2A --

Column 22,
Line 35, change "horseradis-hperoxidase" to -- horseradish-peroxidase --
Line 57, change "favorablephenotype" to -- favorable phenotype --

Signed and Sealed this

Eighteenth Day of November, 2003

JAMES E. ROGAN
*Director of the United States Patent and Trademark Office*

SEQUENCE LISTING

<160> NUMBER OF SEQ ID NOS: 29

<210> SEQ ID NO 1
<211> LENGTH: 35
<212> TYPE: DNA
<213> ORGANISM: Artificial Sequence
<220> FEATURE:
<223> OTHER INFORMATION: Description of Artificial  Sequence: primer
      DBPpcr1

<400> SEQUENCE: 1
cgggatccgc caccatggcc agtcgggaag aggag                                      35

<210> SEQ ID NO 2
<211> LENGTH: 33
<212> TYPE: DNA
<213> ORGANISM: Artificial Sequence
<220> FEATURE:
<223> OTHER INFORMATION: Description of Artificial  Sequence: primer
      DBPpcr2

<400> SEQUENCE: 2
cggaattctt aaaaatcaaa ggggttctgc cgc                                        33

<210> SEQ ID NO 3
<211> LENGTH: 23
<212> TYPE: DNA
<213> ORGANISM: Artificial Sequence
<220> FEATURE:
<223> OTHER INFORMATION: Description of Artificial  Sequence: oligo-
      linker containing PacI site

<400> SEQUENCE: 3
aattgtctta attaaccgct taa                                                   23

<210> SEQ ID NO 4
<211> LENGTH: 19
<212> TYPE: DNA
<213> ORGANISM: Artificial Sequence
<220> FEATURE:
<223> OTHER INFORMATION: Description of Artificial  Sequence:
      oligonucleotide used to form oligo- linker
      described by SEQ. ID. NO.: 3

<400> SEQUENCE: 4
aattgtctta attaaccgc                                                        19

<210> SEQ ID NO 5
<211> LENGTH: 19
<212> TYPE: DNA
<213> ORGANISM: Artificial Sequence
<220> FEATURE:
<223> OTHER INFORMATION: Description of Artificial  Sequence:
      oligonucleotide used to form oligo- linker
      described by SEQ. ID. NO.: 3

<400> SEQUENCE: 5
aattgcggtt aattaagac                                                        19

<210> SEQ ID NO 6
<211> LENGTH: 23
<212> TYPE: DNA
<213> ORGANISM: Artificial Sequence
<220> FEATURE:
<223> OTHER INFORMATION: Description of Artificial  Sequence: primer
      DE2A.SnaBI

<400> SEQUENCE: 6
ggcgtacgta gccctgtcga aag                                           23

<210> SEQ ID NO 7
<211> LENGTH: 35
<212> TYPE: DNA
<213> ORGANISM: Artificial Sequence
<220> FEATURE:
<223> OTHER INFORMATION: Description of Artificial  Sequence: primer
      DE2A.DBP-start

<400> SEQUENCE: 7
ccaatgcatt cgaagtactt ccttctccta taggc                              35

<210> SEQ ID NO 8
<211> LENGTH: 22
<212> TYPE: DNA
<213> ORGANISM: Artificial Sequence
<220> FEATURE:
<223> OTHER INFORMATION: Description of Artificial  Sequence: primer
      DE2A.DBP-stop

<400> SEQUENCE: 8
ccaatgcata cggcgcagac gg                                            22

<210> SEQ ID NO 9
<211> LENGTH: 21
<212> TYPE: DNA
<213> ORGANISM: Artificial Sequence
<220> FEATURE:
<223> OTHER INFORMATION: Description of Artificial  Sequence: primer
      DE2A.BamHI

<400> SEQUENCE: 9
gaggtggatc ccatggacga g                                             21

<210> SEQ ID NO 10
<211> LENGTH: 27
<212> TYPE: DNA
<213> ORGANISM: Artificial Sequence
<220> FEATURE:
<223> OTHER INFORMATION: Description of Artificial  Sequence: primer
      SV40-1

<400> SEQUENCE: 10
gggggatccg aacttgttta ttgcagc                                       27

<210> SEQ ID NO 11
<211> LENGTH: 25
<212> TYPE: DNA
<213> ORGANISM: Artificial Sequence
<220> FEATURE:
<223> OTHER INFORMATION: Description of Artificial  Sequence: primer
      SV40-2

<400> SEQUENCE: 11
gggagatcta gacatgataa gatac                                         25

<210> SEQ ID NO 12
<211> LENGTH: 27
<212> TYPE: DNA
<213> ORGANISM: Artificial Sequence
<220> FEATURE:
<223> OTHER INFORMATION: Description of Artificial  Sequence: prime
      Ad5-1

```
<400> SEQUENCE: 12
gggagatctg tactgaaatg tgtgggc                                27

<210> SEQ ID NO 13
<211> LENGTH: 24
<212> TYPE: DNA
<213> ORGANISM: Artificial Sequence
<220> FEATURE:
<223> OTHER INFORMATION: Description of Artificial  Sequence: prime
      Ad5-2

<400> SEQUENCE: 13
ggaggctgca gtctccaacg gcgt                                   24

<210> SEQ ID NO 14
<211> LENGTH: 47
<212> TYPE: DNA
<213> ORGANISM: Artificial Sequence
<220> FEATURE:
<223> OTHER INFORMATION: Description of Artificial  Sequence: prime
      LTR-1

<400> SEQUENCE: 14
ctgtacgtac cagtgcactg gcctaggcat ggaaaaatac ataactg          47

<210> SEQ ID NO 15
<211> LENGTH: 63
<212> TYPE: DNA
<213> ORGANISM: Artificial Sequence
<220> FEATURE:
<223> OTHER INFORMATION: Description of Artificial  Sequence: primer
      LTR-2

<400> SEQUENCE: 15
gcggatcctt cgaaccatgg taagcttggt accgctagcg ttaaccgggc g actcagtca   60 atc                                                          63

<210> SEQ ID NO 16
<211> LENGTH: 27
<212> TYPE: DNA
<213> ORGANISM: Artificial Sequence
<220> FEATURE:
<223> OTHER INFORMATION: Description of Artificial  Sequence: primer HSA1

<400> SEQUENCE: 16
gcgccaccat gggcagagcg atggtgg                                27

<210> SEQ ID NO 17
<211> LENGTH: 50
<212> TYPE: DNA
<213> ORGANISM: Artificial Sequence
<220> FEATURE:
<223> OTHER INFORMATION: Description of Artificial  Sequence: primer HSA2

<400> SEQUENCE: 17
gttagatcta agcttgtcga catcgatcta ctaacagtag agatgtagaa        50

<210> SEQ ID NO 18
<211> LENGTH: 32
<212> TYPE: DNA
<213> ORGANISM: Artificial Sequence
<220> FEATURE:
<223> OTHER INFORMATION: Description of Artificial  Sequence: primer used
      for amplification of E. coli Lac Z

<400> SEQUENCE: 18
```

```
ggggtggcca gggtacctct aggcttttgc aa                               32

<210> SEQ ID NO 19
<211> LENGTH: 29
<212> TYPE: DNA
<213> ORGANISM: Artificial Sequence
<220> FEATURE:
<223> OTHER INFORMATION: Description of Artificial  Sequence: primer used
      for amplification of E. coli Lac Z

<400> SEQUENCE: 19 gggggatcc ataaacaagt tcagaatcc                                    29

<210> SEQ ID NO 20
<211> LENGTH: 20
<212> TYPE: DNA
<213> ORGANISM: Artificial Sequence
<220> FEATURE:
<223> OTHER INFORMATION: Description of Artificial  Sequence: primer 1

<400> SEQUENCE: 20 ggtattagg ccaaaggcgc                                              20

<210> SEQ ID NO 21
<211> LENGTH: 33
<212> TYPE: DNA
<213> ORGANISM: Artificial Sequence
<220> FEATURE:
<223> OTHER INFORMATION: Description of Artificial  Sequence: primer 2

<400> SEQUENCE: 21
gatcccatgg aagcttgggt ggcgacccca gcg                              33

<210> SEQ ID NO 22
<211> LENGTH: 36
<212> TYPE: DNA
<213> ORGANISM: Artificial Sequence
<220> FEATURE:
<223> OTHER INFORMATION: Description of Artificial  Sequence: primer 3

<400> SEQUENCE: 22
gatcccatgg ggatccttta ctaagttaca aagcta                           36

<210> SEQ ID NO 23
<211> LENGTH: 19
<212> TYPE: DNA
<213> ORGANISM: Artificial Sequence
<220> FEATURE:
<223> OTHER INFORMATION: Description of Artificial  Sequence: primer 4

<400> SEQUENCE: 23
gtcgctgtag ttggactgg                                              19

<210> SEQ ID NO 24
<211> LENGTH: 20
<212> TYPE: DNA
<213> ORGANISM: Artificial Sequence
<220> FEATURE:
<223> OTHER INFORMATION: Description of Artificial  Sequence: primer 551

<400> SEQUENCE: 24
ccggcaagtc ttgcggcatg                                             20

<210> SEQ ID NO 25
<211> LENGTH: 21
```

```
<212> TYPE: DNA
<213> ORGANISM: Artificial Sequence
<220> FEATURE:
<223> OTHER INFORMATION: Description of Artificial  Sequence: primer 556

<400> SEQUENCE: 25
tagcaggtcg ggcgccgata t                                              21

<210> SEQ ID NO 26
<211> LENGTH: 22
<212> TYPE: DNA
<213> ORGANISM: Artificial Sequence
<220> FEATURE:
<223> OTHER INFORMATION: Description of Artificial  Sequence: primer 553

<400> SEQUENCE: 26
ggctcaggtg gcttttaagc ag                                             22

<210> SEQ ID NO 27
<211> LENGTH: 22
<212> TYPE: DNA
<213> ORGANISM: Artificial Sequence
<220> FEATURE:
<223> OTHER INFORMATION: Description of Artificial  Sequence: primer 554

<400> SEQUENCE: 27
gagttgcgat acacagggtt gc                                             22

<210> SEQ ID NO 28
<211> LENGTH: 20
<212> TYPE: DNA
<213> ORGANISM: Artificial Sequence
<220> FEATURE:
<223> OTHER INFORMATION: Description of Artificial  Sequence: primer 731

<400> SEQUENCE: 28
agtgcgcaga ttaggagcgc                                                20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial  Sequence: primer 734

<400> SEQUENCE: 29
tctgcctata ggagaaggaa                                                20
```